United States Patent
Ahmad

(10) Patent No.: US 10,329,273 B2
(45) Date of Patent: *Jun. 25, 2019

(54) TETRAZOLONE-SUBSTITUTED DIHYDROPYRIDINONE MGAT2 INHIBITORS

(71) Applicant: BRISTOL-MYERS SQUIBB COMPANY, Princeton, NJ (US)

(72) Inventor: Saleem Ahmad, Wall, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/117,107

(22) Filed: Aug. 30, 2018

(65) Prior Publication Data

US 2018/0370945 A1    Dec. 27, 2018

Related U.S. Application Data

(63) Continuation of application No. 15/866,871, filed on Jan. 10, 2018, now Pat. No. 10,093,650, which is a continuation of application No. 15/602,515, filed on May 23, 2017, now Pat. No. 9,896,431, which is a continuation of application No. 15/123,773, filed as application No. PCT/US2015/018870 on Mar. 15, 2015, now Pat. No. 9,688,656.

(60) Provisional application No. 61/949,490, filed on Mar. 7, 2014.

(51) Int. Cl.
| | |
|---|---|
| *A61K 45/06* | (2006.01) |
| *C07D 401/04* | (2006.01) |
| *C07D 401/14* | (2006.01) |
| *C07D 409/14* | (2006.01) |
| *C07D 417/14* | (2006.01) |
| *A61K 31/4439* | (2006.01) |

(52) U.S. Cl.
CPC ........ *C07D 401/04* (2013.01); *A61K 31/4439* (2013.01); *A61K 45/06* (2013.01); *C07D 401/14* (2013.01); *C07D 409/14* (2013.01); *C07D 417/14* (2013.01)

(58) Field of Classification Search
None
See application file for complete search history.

(56) References Cited

U.S. PATENT DOCUMENTS

| | | |
|---|---|---|
| 8,791,091 B2 | 7/2014 | Turdi et al. |
| 9,187,424 B1 | 11/2015 | Turdi et al. |
| 9,365,558 B2 | 6/2016 | Ahmad et al. |
| 9,663,466 B2 | 5/2017 | Turdi et al. |
| 9,701,672 B2 | 7/2017 | Meng et al. |
| 9,901,572 B2 | 2/2018 | Turdi et al. |

OTHER PUBLICATIONS

Okawa, M. et al., "Role of MGAT2 and DGAT1 in the release of gut peptides after triglyceride ingestion", Biochemical and Biophysical Research Communications, vol. 390, pp. 377-381 (2009).

Seethala, R., et al., "A simple homogeneous scintillation proximity assay for acyl-coenzyme A:diacylglycerol acyltransferase", Analytical Biochemistry, vol. 383, pp. 144-150 (2008).

Yen, Chi-Liang Eric, et al., "Deficiency of the intestinal enzyme acyl CoA:monoacylglycerol acytransferase-2 protects mice from metabolic disorders induced by high-fat feeding", Nature Medicine, vol. 15(4), pp. 442-446 (2009).

Yen, Chi-Liang Eric, et al., "MGAT2, a Monoacylglycerol Acyltransferase Expressed in the Small Intestine", The Journal of Biological Chemistry, vol. 278(20), pp. 18532-18537 (2003).

*Primary Examiner* — Karl J Puttlitz
(74) *Attorney, Agent, or Firm* — Jing G. Sun

(57) ABSTRACT

The present invention provides compounds of Formula (I):

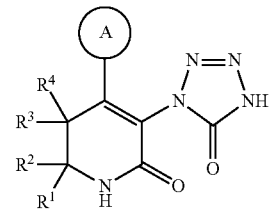

a stereoisomer, a tautomer, a pharmaceutically acceptable salt, a polymorph, a solvate thereof, wherein all of the variables are as defined herein. These compounds are monoacylglycerol acyltransferase type 2 (MGAT2) inhibitors which may be used as medicaments.

22 Claims, No Drawings

TETRAZOLONE-SUBSTITUTED DIHYDROPYRIDINONE MGAT2 INHIBITORS

CROSS-REFERENCE TO RELATED APPLICATIONS

This application is a continuation of U.S. patent application Ser. No. 15/866,871, filed Jan. 10, 2018, now allowed, which is a continuation of U.S. patent application Ser. No. 15/602,515, filed May 23, 2017, now U.S. Pat. No. 9,896,431 issued Feb. 20, 2018, which is a continuation of U.S. patent application Ser. No. 15/123,773, filed Sep. 6, 2016, now U.S. Pat. No. 9,688,656, issued Jun. 27, 2017, which is a 371 of International Application No. PCT/US2015/018870 filed on Mar. 5, 2015, which claims priority to U.S. Provisional Application Ser. No. 61/949,490, filed Mar. 7, 2014; the entire content of which is incorporated herein by reference.

FIELD OF THE INVENTION

The present invention provides novel tetrazolone-substituted dihydropyridinone compounds, and analogues thereof, which are MGAT2 inhibitors, compositions containing them, and methods of using them, for example, for the treatment of diabetes, obesity, dyslipidemia and related conditions.

BACKGROUND OF THE INVENTION

The prevalence of obesity and diabetes is increasing at an alarming rate.

According to WHO, in 2008, 70% of the U.S. adult population was overweight, and among them 33% were obese. Parallel to the explosive number of people becoming overweight and obese, in 2008, it was estimated that 12.3% of the U.S. population had elevated blood glucose [http://www.who.int/diabetes/facts/en/]. The obesity/diabetes epidemic is not unique to the U.S. According to WHO (Fact Sheet No. 312, September 2012), 347 million people worldwide have diabetes. Treating obesity and improving glycemic control effectively and safely remain major challenges for modern medicine.

Monoacylglycerol acyltransferase 2 (MGAT2) has emerged as an attractive target for the treatment of obesity and type II diabetes [Yen, C. L. et al., *Nat. Med.*, 15(4):442-446 (2009)]. MGAT2 is highly and selectively expressed in the small intestine where it exerts a pivotal role in the monoacylglycerol-pathway for the absorption of dietary fat. When dietary fat is ingested, pancreatic lipase digests triglycerides into free fatty acids and 2-monoacylglycerol, which are absorbed by intestinal epithelial enterocytes. Once inside enterocytes, free fatty acids and 2-monoacylglycerol are used as building blocks to resynthesize triglycerides by two sequential acylation steps; first by MGAT and then by DGAT enzyme reactions. Triglycerides are then incorporated into chylomicrons and secreted into lymph to be utilized as an energy supply for the body. MGAT2 knockout mice exhibit a healthy metabolic phenotype and show resistance to high-fat diet induced obesity, improvement in insulin sensitivity and decreased fat accumulation in liver and adipose tissue. In addition, genetic deletion of MGAT2 produces mice with increased levels of GLP1 [Yen, C. L. et al., *Nat. Med.*, 15(4):442-446 (2009)]. Taken together, these data show that MGAT2 inhibitors hold promise to treat metabolic disorders such as obesity, type II diabetes and dyslipidemia.

SUMMARY OF THE INVENTION

The present invention provides tetrazolone-substituted dihydropyridinone compounds, and analogues thereof, which are useful as MGAT2 inhibitors, including stereoisomers, tautomers, pharmaceutically acceptable salts, polymorphs, or solvates thereof.

The present invention also provides processes and intermediates for making the compounds of the present invention or stereoisomers, tautomers, pharmaceutically acceptable salts, polymorphs, or solvates thereof.

The present invention also provides pharmaceutical compositions comprising a pharmaceutically acceptable carrier and at least one of the compounds of the present invention or stereoisomers, tautomers, pharmaceutically acceptable salts, polymorphs, or solvates thereof.

The compounds of the invention may be used in the treatment of multiple diseases or disorders associated with MGAT2, such as diabetes, obesity, dyslipidemia and related conditions, such as microvascular and macrovascular complications associated with diabetes, cardiovascular diseases, Metabolic Syndrome and its component conditions, disorders of glucose and lipid metabolism and other maladies.

The compounds of the invention may be used in therapy.

The compounds of the invention may be used for the manufacture of a medicament for the treatment of multiple diseases or disorders associated with MGAT2.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

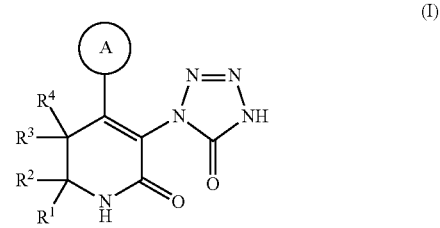

(I)

or a stereoisomer, a tautomer, a pharmaceutically acceptable salt, a polymorph, a solvate or a hydrate thereof, wherein:

ring A is independently phenyl or a 5- to 6-membered heteroaryl comprising carbon atoms and 1-4 heteroatoms selected from N, $NR^e$, O and S; wherein said phenyl and heteroaryl are substituted with 0-1 $R^6$ and 0-2 $R^7$;

$R^1$ is independently selected from: $-(CH_2)_m-(C_{3-6}$ carbocycle substituted with 0-2 $R^b$ and 0-2 $R^g$), $-(CH_2)_m$-(5- to 6-membered heteroaryl comprising carbon atoms and 1-4 heteroatoms selected from N, $NR^e$, O and S; wherein said heteroaryl is substituted with 0-1 $R^b$ and 0-2 $R^g$), and (a $C_{1-12}$ hydrocarbon chain substituted with 0-3 $R^a$; wherein said hydrocarbon chain may be straight or branched, saturated or unsaturated);

$R^2$ is independently selected from: $C_{1-4}$ alkyl, $C_{3-4}$ cycloalkyl, and $C_{1-4}$ haloalkyl;

$R^3$ is independently selected from: H, F, $C_{1-4}$ alkyl and CN;

$R^4$ is independently selected from: H, F, and $C_{1-4}$ alkyl;

$R^3$ and $R^4$ may be combined with the carbon atom to which they are attached to form a 3- to 6-membered carbocycle;

$R^6$ is independently selected from: halogen, $C_{1-6}$ alkyl substituted with 0-2 $R^h$, $C_{1-4}$ alkoxy, $C_{1-4}$ haloalkyl, $C_{1-4}$ haloalkoxy, $CO(C_{1-4}$ alkyl), $-(CH_2)_m-C_{3-6}$ carbocycle, $-(CH_2)_m-NR^fR^i$, CN, $OR^i$, $SR^i$, and (a 4- to 6-membered heterocycle comprising carbon atoms and 1-4 heteroatoms selected from N, $NR^e$, O, and S);

$R^7$ is independently selected from: halogen, $C_{1-4}$ alkyl, $C_{1-4}$ alkoxy, $C_{1-4}$ haloalkyl, and $C_{1-4}$ haloalkoxy;

alternatively, $R^6$ and $R^7$, together with the carbon atoms to which they are attached, combine to form a 5- to 6-membered carbocyclic ring or a 5- to 6-membered heterocyclic ring comprising carbon atoms and 1-3 heteroatoms selected from N, $NR^e$, O, and S; wherein said heterocycle is substituted with 0-2 $R^g$;

$R^a$ is, at each occurrence, independently selected from: halogen, OH, $C_{1-6}$ alkoxy, $C_{1-6}$ haloalkyl, $C_{1-6}$ haloalkoxy, $N(C_{1-4}$ alkyl)$_2$, COOH, and $-(CH_2)_n-R^c$;

$R^b$ is, at each occurrence, independently selected from: halogen, OH, $C_{1-10}$ alkyl, $C_{1-10}$ alkoxy, $C_{1-10}$ haloalkyl, $C_{1-10}$ haloalkoxy, $C_{1-10}$ alkylthio, $C_{1-10}$ haloalkylthio, $N(C_{1-4}$ alkyl)$_2$, $-CONH(C_{4-20}$ alkyl), $-CONH(C_{4-20}$ haloalkyl), $-O(CH_2)_sO(C_{1-6}$ alkyl), $-O(CH_2)_sO(C_{1-6}$ haloalkyl), $R^c$, and $-(CH_2)_n-(O)_t-(CH_2)_mR^c$;

$R^c$ is, at each occurrence, independently selected from: $C_{3-6}$ cycloalkyl substituted with 0-2 $R^d$, $C_{3-6}$ cycloalkenyl substituted with 0-2 $R^d$, $-(CH_2)_m$-(phenyl substituted with 0-3 $R^d$), and (a 5- to 6-membered heterocycle comprising carbon atoms and 1-4 heteroatoms selected from N, $NR^e$, O, and S; wherein said heterocycle is substituted with 0-2 $R^d$);

$R^d$ is, at each occurrence, independently selected from: halogen, OH, CN, $NO_2$, $C_{1-4}$ alkyl, $C_{1-4}$ alkoxy, $C_{1-4}$ haloalkyl, $C_{1-4}$ haloalkoxy, tetrazolyl, OBn and phenyl;

$R^e$ is, at each occurrence, independently selected from: H, $C_{1-8}$ alkyl, $C_{1-8}$ haloalkyl, $-(CH_2)_n-C_{3-6}$ carbocycle, $CO(C_{1-4}$ alkyl) and COBn;

$R^f$ is, at each occurrence, independently selected from: H and $C_{1-4}$ alkyl;

$R^g$ is, at each occurrence, independently selected from: halogen, $C_{1-4}$ alkyl, $C_{1-4}$ alkoxy, $C_{1-4}$ haloalkyl, and $C_{1-4}$ haloalkoxy;

$R^h$ is, at each occurrence, independently selected from: OH, halogen, $C_{1-4}$ alkyl, $C_{1-4}$ alkoxy, $C_{1-4}$ haloalkyl, and $C_{1-4}$ haloalkoxy;

$R^i$ is, at each occurrence, independently selected from the group consisting of $C_{1-4}$ alkyl, $C_{3-4}$ cycloalkyl and phenyl;

n, at each occurrence, is independently 0 or 1;

m, at each occurrence, is independently 0, 1, 2, 3, or 4;

s, at each occurrence, is independently 1, 2, or 3; and t, at each occurrence, is independently 0 or 1.

In a second aspect, the present invention provides a compound of Formula (I) or a stereoisomer, a tautomer, a pharmaceutically acceptable salt, a polymorph, a solvate or a hydrate thereof, within the scope of the first aspect, wherein:

$R^1$ is independently selected from: ($C_{3-6}$ carbocycle substituted with 0-2 $R^b$ and 0-2 $R^g$), and (a 5- to 6-membered heteroaryl comprising carbon atoms and 1-4 heteroatoms selected from N, $NR^e$, O and S; wherein said heteroaryl is substituted with 0-1 $R^b$ and 0-2 $R^g$);

$R^3$ is independently selected from: H, F, $C_{1-4}$ alkyl and CN;

$R^4$ is independently selected from: H, F, and $C_{1-4}$ alkyl;

$R^b$ is, at each occurrence, independently selected from: halogen, $C_{1-10}$ alkyl, $C_{1-10}$ alkoxy, $C_{1-10}$ haloalkyl, $C_{1-10}$ haloalkoxy, $C_{1-10}$ alkylthio, $C_{1-10}$ haloalkylthio, $N(C_{1-4}$ alkyl)$_2$, $-CONH(C_{4-20}$ alkyl), $-CONH(C_{4-20}$ haloalkyl), $-O(CH_2)_sO(C_{1-6}$ alkyl), $-O(CH_2)_sO(C_{1-6}$ haloalkyl), $R^c$, and $-(CH_2)_n-(O)_t-(CH_2)_mR^c$; and $R^d$ is, at each occurrence, independently selected from: halogen, $C_{1-4}$ alkyl, $C_{1-4}$ alkoxy, $C_{1-4}$ haloalkyl, $C_{1-4}$ haloalkoxy, tetrazolyl, OBn and phenyl.

In a third aspect, the present invention provides a compound of Formula (I) or a stereoisomer, a tautomer, a pharmaceutically acceptable salt, a polymorph, a solvate or a hydrate thereof, within the scope of the first or second aspect, wherein:

ring A is independently selected from phenyl, pyrrolyl, thienyl, thiazolyl, pyrazolyl, pyridyl, and pyrimidinyl; wherein each ring moiety is substituted with 0-1 $R^6$ and 0-2 $R^7$; and alternatively, $R^6$ and $R^7$, together with the carbon atoms to which they are attached, combine to form a 6-membered carbocyclic ring.

In a fourth aspect, the present invention includes a compound of Formula (I), or a stereoisomer, a tautomer, a pharmaceutically acceptable salt, a polymorph, a solvate or a hydrate thereof, within the scope of any of the above aspects, wherein:

ring A is independently selected from:

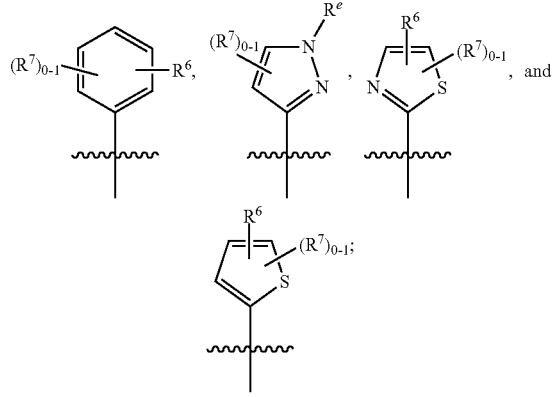

$R^1$ is independently selected from: (phenyl substituted with 1 $R^b$ and 0-2 $R^g$), and (a 5-membered heteroaryl comprising carbon atoms and 1-2 heteroatoms selected from N, $NR^e$, O and S; wherein said heteroaryl is substituted with 0-1 $R^b$ and 0-2 $R^g$);

$R^2$ is independently selected from: $C_{1-4}$ alkyl and $C_{1-4}$ haloalkyl;

$R^6$ is independently selected from: halogen, $C_{1-6}$ alkyl with 0-1 OH, $C_{1-4}$ alkoxy, $C_{1-4}$ haloalkoxy, $CO(C_{1-4}$ alkyl), $N(C_{1-4}$ alkyl)$_2$, and $-(CH_2)_{0-1}-C_{3-6}$ cycloalkyl;

$R^7$ is independently selected from: halogen, $C_{1-4}$ alkyl and $C_{1-4}$ alkoxy;

alternatively, $R^6$ and $R^7$, together with the carbon atoms to which they are attached, combine to form a 6-membered carbocyclic ring;

$R^b$ is, at each occurrence, independently selected from: halogen, $C_{1-8}$ alkyl, $C_{1-8}$ alkoxy, $C_{1-8}$ haloalkyl, $C_{1-10}$ haloalkoxy, and phenoxy;

$R^e$ is, at each occurrence, independently selected from: $C_{1-6}$ alkyl, $C_{1-8}$ haloalkyl, and $—(CH_2)_n—C_{3-6}$ carbocycle; and $R^g$ is, at each occurrence, independently selected from: halogen, $C_{1-4}$ alkyl, $C_{1-4}$ alkoxy, $C_{1-4}$ haloalkyl, and $C_{1-4}$ haloalkoxy.

In a fifth aspect, the present invention provides a compound of Formula (IIa), (IIb), (IIc), (IId), or (IIe):

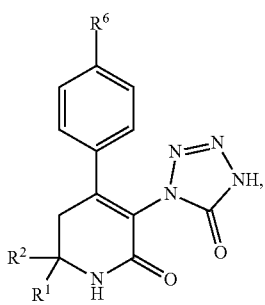
(IIa)

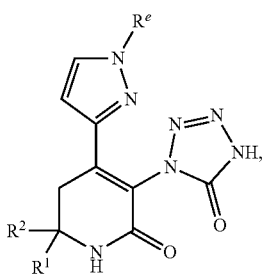
(IIb)

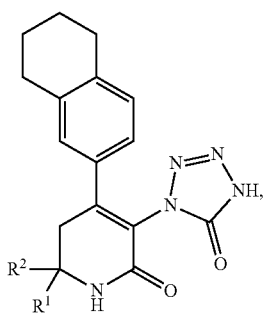
(IIc)

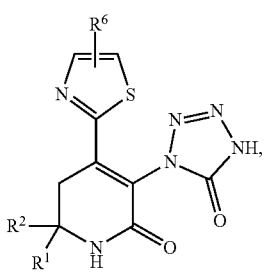
(IId)

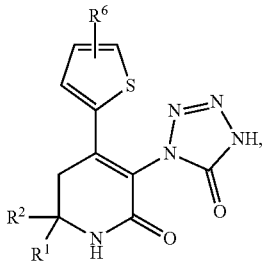
(IIe)

or a stereoisomer, a tautomer, a pharmaceutically acceptable salt, a polymorph, a solvate or a hydrate thereof, within the scope of any of the above aspects, wherein:

$R^1$ is independently selected from:

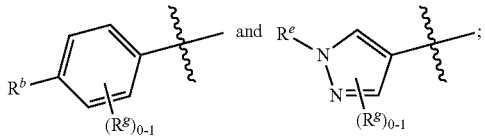

$R^2$ is independently selected from: $CF_3$ and $CH_3$;
$R^6$ is independently selected from: halogen, $C_{1-4}$ alkyl substituted with 0-1 OH, $C_{1-4}$ alkoxy, $C_{1-4}$ haloalkoxy, $CO(C_{1-4}$ alkyl), and $—(CH_2)_{0-1}—C_{3-4}$ cycloalkyl;
$R^b$ is independently selected from: $—(CH_2)_{1-6}CF_3$, $—(CH_2)_{1-4}CF_2CF_3$, $—O(CH_2)_{1-6}CF_3$, and $—O(CH_2)_{1-4}CF_2CF_3$;
$R^e$ is, at each occurrence, independently selected from: $C_{1-4}$ alkyl, $—(CH_2)_{1-6}CF_3$, and $—(CH_2)_{0-1}—C_{3-4}$ cycloalkyl; and
$R^g$ is independently halogen.

In another aspect, the present invention provides a compound of Formula (IIa):

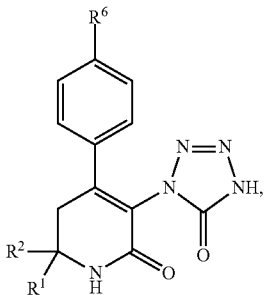
(IIa)

or a stereoisomer, a tautomer, a pharmaceutically acceptable salt, a polymorph, a solvate or a hydrate thereof, within the scope of any of the above aspects, wherein:

$R^1$ is independently selected from:

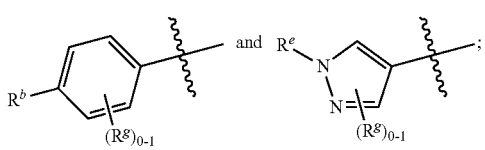

$R^2$ is independently selected from: $CF_3$ and $CH_3$;

$R^6$ is independently selected from: halogen, $C_{1-4}$ alkyl substituted with 0-1 OH, $C_{1-4}$ alkoxy, $C_{1-4}$ haloalkoxy, $CO(C_{1-4}$ alkyl), and —$(CH_2)_{0-1}$—$C_{3-4}$ cycloalkyl;

$R^b$ is independently selected from: —$(CH_2)_{1-6}CF_3$, —$(CH_2)_{1-4}CF_2CF_3$, —$O(CH_2)_{1-6}CF_3$, and —$O(CH_2)_{1-4}CF_2CF_3$;

$R^e$ is, at each occurrence, independently selected from: $C_{1-4}$ alkyl, —$(CH_2)_{1-6}CF_3$, and —$(CH_2)_{0-1}$—$C_{3-4}$ cycloalkyl; and $R^g$ is independently halogen.

In another aspect, the present invention provides a compound of Formula (IIb):

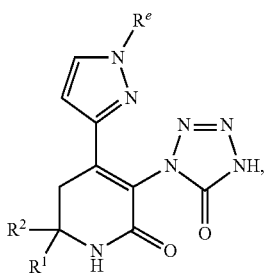
(IIb)

or a stereoisomer, a tautomer, a pharmaceutically acceptable salt, a polymorph, a solvate or a hydrate thereof, within the scope of any of the above aspects, wherein:

$R^1$ is independently selected from:

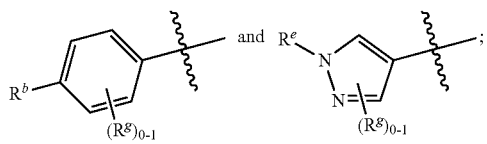

$R^2$ is independently selected from: $CF_3$ and $CH_3$;

$R^6$ is independently selected from: halogen, $C_{1-4}$ alkyl substituted with 0-1 OH, $C_{1-4}$ alkoxy, $C_{1-4}$ haloalkoxy, $CO(C_{1-4}$ alkyl), and —$(CH_2)_{0-1}$—$C_{3-4}$ cycloalkyl;

$R^b$ is independently selected from: —$(CH_2)_{1-6}CF_3$, —$(CH_2)_{1-4}CF_2CF_3$, —$O(CH_2)_{1-6}CF_3$, and —$O(CH_2)_{1-4}CF_2CF_3$;

$R^e$ is, at each occurrence, independently selected from: $C_{1-4}$ alkyl, —$(CH_2)_{1-6}CF_3$, and —$(CH_2)_{0-1}$—$C_{3-4}$ cycloalkyl; and $R^g$ is independently halogen.

In another aspect, the present invention provides a compound of Formula (IIc):

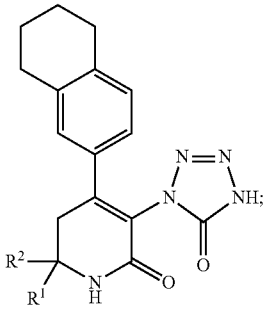
(IIc)

or a stereoisomer, a tautomer, a pharmaceutically acceptable salt, a polymorph, a solvate or a hydrate thereof, within the scope of any of the above aspects, wherein:

$R^1$ is independently selected from:

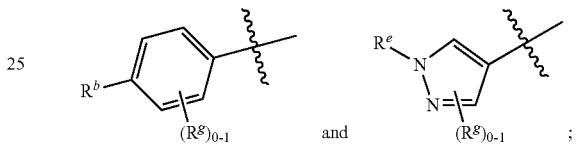

$R^2$ is independently selected from: $CF_3$ and $CH_3$;

$R^6$ is independently selected from: halogen, $C_{1-4}$ alkyl substituted with 0-1 OH, $C_{1-4}$ alkoxy, $C_{1-4}$ haloalkoxy, $CO(C_{1-4}$ alkyl), and —$(CH_2)_{0-1}$—$C_{3-4}$ cycloalkyl;

$R^b$ is independently selected from: —$(CH_2)_{1-6}CF_3$, —$(CH_2)_{1-4}CF_2CF_3$, —$O(CH_2)_{1-6}CF_3$, and —$O(CH_2)_{1-4}CF_2CF_3$;

$R^e$ is, at each occurrence, independently selected from: $C_{1-4}$ alkyl, —$(CH_2)_{1-6}CF_3$, and —$(CH_2)_{0-1}$—$C_{3-4}$ cycloalkyl; and $R^g$ is independently halogen.

In another aspect, the present invention provides a compound of Formula (IId):

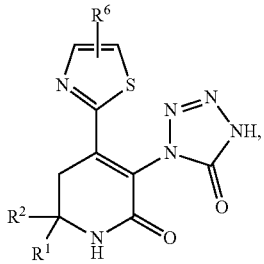
(IId)

or a stereoisomer, a tautomer, a pharmaceutically acceptable salt, a polymorph, a solvate or a hydrate thereof, within the scope of any of the above aspects, wherein:

$R^1$ is independently selected from:

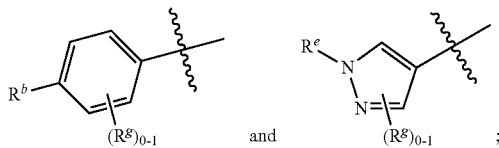

and $R^2$ is independently selected from: $CF_3$ and $CH_3$;
$R^6$ is independently selected from: halogen, $C_{1-4}$ alkyl substituted with 0-1 OH, $C_{1-4}$ alkoxy, $C_{1-4}$ haloalkoxy, $CO(C_{1-4}$ alkyl), and $-(CH_2)_{0-1}-C_{3-4}$ cycloalkyl;
$R^b$ is independently selected from: $-(CH_2)_{1-6}CF_3$, $-(CH_2)_{1-4}CF_2CF_3$, $-O(CH_2)_{1-6}CF_3$, and $-O(CH_2)_{1-4}CF_2CF_3$;
$R^e$ is, at each occurrence, independently selected from: $C_{1-4}$ alkyl, $-(CH_2)_{1-6}CF_3$, and $-(CH_2)_{0-1}-C_{3-4}$ cycloalkyl; and
$R^g$ is independently halogen.

In another aspect, the present invention provides a compound of Formula (IId):

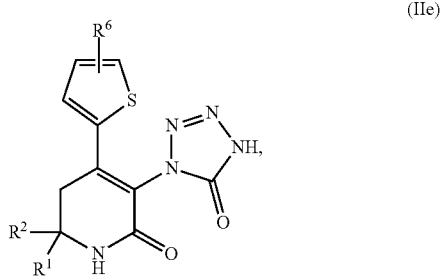

(IIe)

or a stereoisomer, a tautomer, a pharmaceutically acceptable salt, a polymorph, a solvate or a hydrate thereof, within the scope of any of the above aspects, wherein:
$R^1$ is independently selected from:

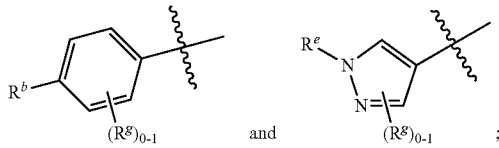

and $R^2$ is independently selected from: $CF_3$ and $CH_3$;
$R^6$ is independently selected from: halogen, $C_{1-4}$ alkyl substituted with 0-1 OH, $C_{1-4}$ alkoxy, $C_{1-4}$ haloalkoxy, $CO(C_{1-4}$ alkyl), and $-(CH_2)_{0-1}-C_{3-4}$ cycloalkyl;
$R^b$ is independently selected from: $-(CH_2)_{1-6}CF_3$, $-(CH_2)_{1-4}CF_2CF_3$, $-O(CH_2)_{1-6}CF_3$, and $-O(CH_2)_{1-4}CF_2CF_3$;
$R^e$ is, at each occurrence, independently selected from: $C_{1-4}$ alkyl, $-(CH_2)_{1-6}CF_3$, and $-(CH_2)_{0-1}-C_{3-4}$ cycloalkyl; and
$R^g$ is independently halogen.

In a sixth aspect, the present invention includes a compound of Formula (I), (IIa), (IIb) or (IIc), or a stereoisomer, a tautomer, a pharmaceutically acceptable salt, a polymorph, a solvate or a hydrate thereof, within the scope of any of the above aspects, wherein:

$R^1$ is

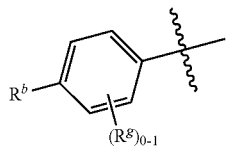

.

In a seventh aspect, the present invention provides a compound selected from the exemplified examples or a stereoisomer, a tautomer, a pharmaceutically acceptable salt, a polymorph, a solvate or a hydrate thereof.

In another aspect, the present invention provides a compound selected from any subset list of compounds or a single compound from the exemplified examples within the scope of any of the above aspects.

In another embodiment, the compounds of the present invention have hMGAT2 $IC_{50}$ values $\leq 1$ μM, using the MGAT2 LCMS assay.

In another embodiment, the compounds of the present invention have hMGAT2 $IC_{50}$ values $\leq 0.5$ μM, using the MGAT2 LCMS assay.

In another embodiment, the compounds of the present invention have hMGAT2 $IC_{50}$ values $\leq 0.1$ μM, using the MGAT2 LCMS assay.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a pharmaceutical composition further comprising additional therapeutic agent(s). In a preferred embodiment, the present invention provides pharmaceutical composition, wherein the additional therapeutic agent is, for example, a dipeptidyl peptidase-IV (DPP4) inhibitor (for example a member selected from saxagliptin, sitagliptin, vildagliptin and alogliptin).

In another embodiment, the present invention provides a method for the treatment of multiple diseases or disorders associated with MGAT2, comprising administering to a patient in need of such treatment a therapeutically effective amount of at least one of the compounds of the present invention, alone, or, optionally, in combination with another compound of the present invention and/or at least one other type of therapeutic agent.

Examples of diseases or disorders associated with the activity of the MGAT2 that can be prevented, modulated, or treated according to the present invention include, but are not limited to, diabetes, hyperglycemia, impaired glucose tolerance, gestational diabetes, insulin resistance, hyperinsulinemia, nonalcoholic fatty liver disease (NAFLD) including nonalcoholic steatohepatitis (NASH), retinopathy, neuropathy, nephropathy, delayed wound healing, atherosclerosis and its sequelae, abnormal heart function, myocardial ischemia, stroke, Metabolic Syndrome, hypertension, obesity, dyslipidemia, dyslipidemia, hyperlipidemia, hypertriglyceridemia, hypercholesterolemia, low high-density lipoprotein (HDL), high low-density lipoprotein (LDL), non-cardiac ischemia, lipid disorders, and glaucoma.

In another embodiment, the present invention provides a method for the treatment of diabetes, hyperglycemia, gestational diabetes, obesity, dyslipidemia, and hypertension, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of diabetes, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of hyperglycemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of obesity, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of dyslipidemia, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for the treatment of hypertension, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of multiple diseases or disorders associated with MGAT2.

In another embodiment, the present invention also provides the use of a compound of the present invention for the manufacture of a medicament for the treatment of multiple diseases or disorders associated with MGAT2.

In another embodiment, the present invention provides a method for the treatment of multiple diseases or disorders associated with MGAT2, comprising administering to a patient in need thereof a therapeutically effective amount of a first and second therapeutic agent, wherein the first therapeutic agent is a compound of the present invention. Preferably, the second therapeutic agent, for example, dipeptidyl peptidase-IV (DPP4) inhibitor (for example a member selected from saxagliptin, sitagliptin, vildagliptin, linagliptin and alogliptin).

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of multiple diseases or disorders associated with MGAT2.

Where desired, the compound of the present invention may be used in combination with one or more other types of anti-diabetic agents and/or one or more other types of therapeutic agents which may be administered orally in the same dosage form, in a separate oral dosage form or by injection. The other type of anti-diabetic agent that may be optionally employed in combination with the MGAT2 inhibitor of the present invention may be one, two, three or more anti-diabetic agents or antihyperglycemic agents which may be administered orally in the same dosage form, in a separate oral dosage form, or by injection to produce an additional pharmacological benefit.

The anti-diabetic agents used in the combination with the MGAT2 inhibitor of the present invention include, but are not limited to, insulin secretagogues or insulin sensitizers, other MGAT2 inhibitors, or other anti-diabetic agents. These agents include, but are not limited to, dipeptidyl peptidase IV (DPP4) inhibitors (for example, sitagliptin, saxagliptin, alogliptin, linagliptin and vildagliptin), biguanides (for example, metformin and phenformin), sulfonyl ureas (for example, glyburide, glimepiride and glipizide), glucosidase inhibitors (for example, acarbose, miglitol), PPARγ agonists such as thiazolidinediones (for example, rosiglitazone and pioglitazone), PPAR α/γ dual agonists (for example, muraglitazar, tesaglitazar and aleglitazar), glucokinase activators, GPR40 receptor modulators (e.g., TAK-875), GPR119 receptor modulators (for example, MBX-2952, PSN821, and APD597), sodium-glucose transporter-2 (SGLT2) inhibitors (for example, dapagliflozin, canagliflozin and remagliflozin), 11β-HSD-1 inhibitors (for example MK-0736, BI35585, BMS-823778, and LY2523199), amylin analogs such as pramlintide, leptin signaling modulators (for example, metreleptin), and/or insulin.

The MGAT2 inhibitor of the present invention may also be optionally employed in combination with one or more hypophagic and/or weight-loss agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The compounds of the present invention may also be employed in combination with an agonist of the glucagon-like peptide-1 receptor (GLP-1 R), such as exenatide, liraglutide, GPR-1(1-36) amide, GLP-1 (7-36) amide, GLP-1(7-37), which may be administered via injection, intranasal, or by transdermal or buccal devices.

The MGAT2 inhibitor of the present invention may also be optionally employed in combination with one or more other types of therapeutic agents, such as DGAT inhibitors, LDL lowering drugs such as statins (inhibitors of HMG CoA reductase) or inhibitors of cholesterol absorption, modulators of PCSK9, drugs that increase HDL such as CETP inhibitors.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. The term "stereoisomer(s)" refers to compound(s) which have identical chemical constitution, but differ with regard to the arrangement of the atoms or groups in space. Unless otherwise indicated, all chiral (enantiomeric and diastereomeric) and racemic forms are within the scope of the invention. The term "chiral" refers to molecules which have the property of non-superimposability of the mirror image partner, while the term "achiral" refers to molecules which are superimposable on their mirror image partner. The terms "racemic mixture" and "racemate" refer to an equimolar mixture of two enantiomeric species, devoid of optical activity.

Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms.

The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization.

Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

Unless otherwise indicated, any heteroatom with unsatisfied valences is assumed to have hydrogen atoms sufficient to satisfy the valences.

As used herein, the term "alkyl" or "alkylene" is intended to include both branched and straight-chain saturated aliphatic hydrocarbon groups having the specified number of carbon atoms. For examples, "$C_1$ to $C_{12}$ alkyl" or "$C_{1-12}$ alkyl" (or alkylene), is intended to include $C_1$, $C_2$, $C_3$, $C_4$, $C_5$, $C_6$, $C_7$, $C_8$, $C_9$, $C_{10}$, $C_{11}$ and $C_{12}$ alkyl groups; "$C_4$ to $C_{18}$ alkyl" or "$C_{4-18}$ alkyl" (or alkylene), is intended to include $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, and $C_{18}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

When the term "hydrocarbon chain" is used, it is intended to include "alkyl", "alkenyl" and "alkynyl", unless otherwise specified.

The term "alkoxy" or "alkyloxy" refers to an —O-alkyl group. For example, "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. For example, "$C_3$ to $C_6$ cycloalkyl" or "$C_{3-6}$ cycloalkyl" is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or bicyclic aromatic hydrocarbons, including, for example, phenyl, and naphthyl. Aryl moieties are well known and described, for example, in Lewis, R. J., ed., *Hawley's Condensed Chemical Dictionary*, 15th Edition, J. Wiley & Sons, Inc., New York (2007). "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium ($R_nNH_m+$ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. et al., *Protecting Groups in Organic Synthesis*, 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

Compounds of the present invention can form salts which are also within the scope of this invention. Unless otherwise indicated, reference to an inventive compound is understood to include reference to one or more salts thereof. Pharmaceutically acceptable salts are preferred. However, other salts may be useful, e.g., in isolation or purification steps which may be employed during preparation, and thus, are contemplated within the scope of the invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy,* 22nd Edition, Pharmaceutical Press, London, UK (2012), the disclosure of which is hereby incorporated by reference.

In addition, compounds of the present invention may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5, "Design and Application of Prodrugs", *A Textbook of Drug Design and Development,* pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988);

e) Kakeya, N. et al., *Chem. Pharm. Bull.,* 32:692 (1984); and f) Rautio, J., ed., *Prodrugs and Targeted Delivery (Methods and Principles in Medicinal Chemistry),* Vol. 47, Wiley-VCH (2011).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (Second Edition, reproduced, 2006); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* Third Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, "polymorph(s)" refer to crystalline form(s) having the same chemical structure/composition but different spatial arrangements of the molecules and/or ions forming the crystals. Compounds of the present invention can be provided as amorphous solids or crystalline solids. Lyophilization can be employed to provide the compounds of the present invention as a solid.

All measurements are subject to experimental error and are within the contemplation of the invention.

When the invention is described or characterized by any of the disclosed tables, it is understood that all variations within limitations and/or error margins of the experiments and technology are contemplated.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "L" for microliter or microliters, "N" for normal, "M" for molar, "mmol" for millimole or millimoles, "min" for minute or min, "h" for hour or h, "rt" for room temperature, "RT" for retention time, "atm" for atmosphere, "psi" for pounds per square inch, "conc." for concentrate, "aq" for "aqueous", "sat" or "saturated" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", "Z" and "ee" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Hex hexanes
MeOH methanol
EtOH ethanol
i-PrOH or IPA isopropanol
AcOH or HOAc acetic acid
$Ag_2CO_3$ silver carbonate
AgOAc silver acetate
$CDCl_3$ deutero-chloroform
$CHCl_3$ chloroform
cDNA complementary DNA
DCC N,N'-dicyclohexylcarbodiimide
DIAD diisopropyl azodicarboxylate
DMA dimethylamine
DME dimethylether
DMF dimethyl formamide
DMSO dimethyl sulfoxide
DMAP 4-dimethylaminopyridine
EDTA ethylenediaminetetraacetic acid
EtOAc ethyl acetate
$Et_2O$ diethyl ether
$AlCl_3$ aluminum chloride
Boc tert-butyloxycarbonyl
$CH_2Cl_2$ dichloromethane
$CH_3CN$ or ACN acetonitrile
$Cs_2CO_3$ cesium carbonate
HCl hydrochloric acid
$H_2SO_4$ sulfuric acid
$K_2CO_3$ potassium carbonate
KCN potassium cyanide
mCPBA or m-CPBA meta-chloroperbenzoic acid
Pd/C palladium on carbon
$PhSO_2Cl$ benzenesulfonyl chloride
i-$Pr_2NEt$ diisopropylethylamine
PS polystyrene
SFC Supercritical Fluid Chromatography
$SiO_2$ silica oxide
$SnCl_2$ tin(II) chloride
TBAT tetrabutylammonium triphenydifluorosilicate
TEA triethylamine
TFA trifluoroacetic acid
THF tetrahydrofuran
KOAc potassium acetate
$MgSO_4$ magnesium sulfate
NaCl sodium chloride
NaH sodium hydride
$NaHCO_3$ sodium bicarbonate
NaOH sodium hydroxide
$Na_2SO_3$ sodium sulfite
$Na_2SO_4$ sodium sulfate
$NH_3$ ammonia
$NH_4Cl$ ammonium chloride
$NH_4OH$ ammonium hydroxide
LG leaving group
$Pd_2dba_3$ tris(dibenzylideneacetone)dipalladium(0)
SELECTFLUOR® N-fluoro-N'-methyl-triethylenediamine bis(tetrafluoroborate)

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

Synthesis

The compounds of Formula (I) may be prepared by the exemplary processes described in the following schemes and working examples, as well as relevant published literature procedures that are used by one skilled in the art. Exemplary reagents and procedures for these reactions appear hereinafter and in the working examples. Protection and deprotection in the processes below may be carried out by procedures generally known in the art (see, for example, Wuts, P. G. M. et al., *Protecting Groups in Organic Synthesis*, Fourth Edition, Wiley (2007)). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); Smith, M. B. et al., *March's Advanced Organic Chemistry: Reactions, Mechanisms, and Structure*. Sixth Edition, Wiley & Sons, New York, N.Y. (2007); Katritzky, A. R. et al., eds., *Comprehensive Organic Functional Groups Transformations II*, Second Edition, Elsevier Science Inc., Tarrytown, N.Y. (2004); Larock, R. C., *Comprehensive Organic Transformations*, VCH Publishers, Inc., New York, N.Y. (1999), and references therein.

For example, compounds of Formula (I), where $R^3=R^4=H$ can be prepared according to Scheme 1. α-Bromoketone 1 is combined with triphenylphosphine in a solvent such as THF, dichloromethane or 1,4-dioxane at temperatures between room temperature and reflux. The intermediate triphenylphosphonium bromide is treated with a base, such as NaOH, in a solvent such as methanol and water to form the phosphorous ylide 2. The phosphorous ylide 2 is heated (ca. 60-80° C.) with ketone 3 in a suitable solvent such as THF or DMSO to give α,β-unsaturated ketone 4, which may exist as a mixture of E/Z isomers. Microwave irradiation may be employed to shorten the reaction time. α,β-Unsaturated ketone 4 is treated with concentrated aq $NH_4OH$ in a solvent such as DMSO in a sealed vessel to provide amine 5. Alternatively, alkene 4 may be treated with $NH_3$ in a solvent such as DMSO or DMSO and methanol in a sealed vessel to provide amine 5. Amine 5 can be coupled with acid 6 affording amide 7 using a variety of amide bond forming reactions (e.g., DCC in THF or DMF). The amide 7 can be converted to compound 8 via cyclization in the presence of a base such as piperidine, sodium hydroxide or sodium ethoxide in a suitable solvent such as EtOH at a temperature between room temperature and refluxing temperature. Compound of Formula I can be prepared by removing the protecting group (PG) from compound 8. Intermediates 5, 7 or 8 can optionally be separated into individual enantiomers using chiral separation methods known to those skilled in the art, such as chiral HPLC, chiral SFC, crystallization, etc. and processed further to obtain single enantiomers of Formula (I). Single enantiomers of Formula (I) can alternatively be obtained by separation of racemic Formula (I) using the chiral separation methods outlined above.

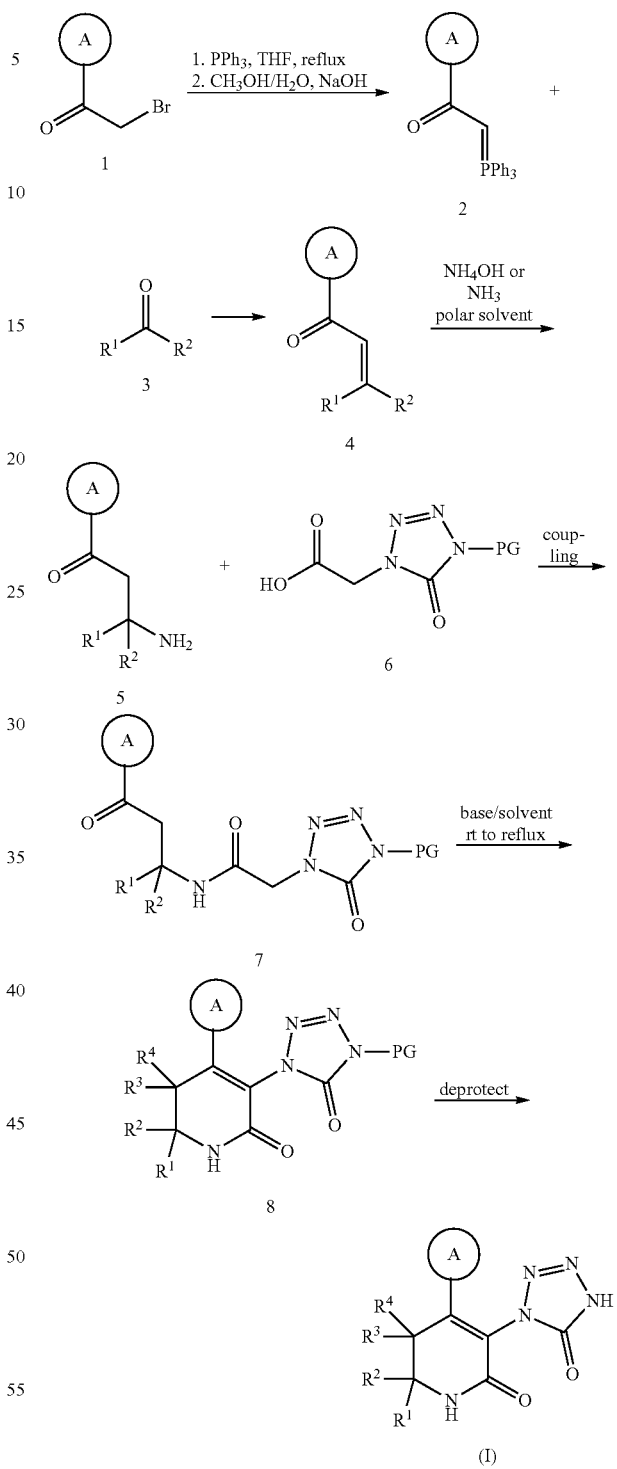

Non-commercial ketones 3, where $R^2=CF_3$, may be prepared from the corresponding aldehyde 9 as shown in Scheme 2. Aldehyde 9 is reacted with trimethyl-(trifluoromethyl)silane in the presence of a fluoride source such as cesium fluoride in a suitable solvent such as dimethoxyethane at room temperature. Other fluoride sources such as potassium hydrogen fluoride or tetrabutylammonium difluorotriphenylsilicate, and other solvents such as THF or acetonitrile and methanol, may also be employed. Trifluoromethyl alcohol 10 is oxidized, for example by using Dess-Martin periodinane or $MnO_2$, in a suitable solvent such as dichloromethane or dichloroethane to afford ketone 3 ($R^2=CF_3$).

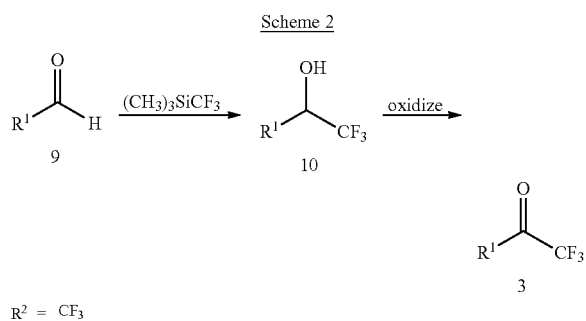

Carboxylic acid 6 may be prepared according to Scheme 3. Reaction of ethyl isocyanatoacetate (11) with sodium azide in the presence of aluminum trichloride affords tetrazolone 12. Alternatively, the tetrazolone 12 can be prepared by treating 11 with trimethylsilyl azide. Compound 6 can be prepared by protecting the tetrazolone functionality in 12 followed by saponification. Commonly used N-protecting groups, known to those skilled in the art, such as 4-methoxybenzyl may be employed.

Lewis acid, such as $Ti(OEt)_4$ or $Ti(OiPr)_4$ in a solvent such as THF at reflux temperature providing E or Z or a mixture of E/Z imines 15. Other Lewis acids, solvents and temperatures may be used as determined by those skilled in the art. Imine 15 is alkylated with ketone 16 in the presence of a base, such as LiHMDS, KHMDS, NaHMDS, or LDA in an aprotic solvent such as THF or ether at a temperature ranging from −78° C. to ambient to provide ketone 17. Ketone 17 can be purified and resolved into individual isomers, for example, by chromatography prior to removal of the sulfinyl group. Other metal enolates (such as titanium enolate), solvents, and temperatures may be used as determined by those skilled in the art (Tang, T. P. et al., *J. Org. Chem.*, 64:12-13 (1999), *J. Org. Chem.*, 67:7819-7832 (2002)). Chiral S- or R-2-methylpropane-2-sulfinamide can be optionally used to generate each of the optically pure enantiomers of imine 15 that can allow for chiral induction to prepare diastereomerically enriched ketone 17. In these cases, the product mixture can be further purified by chromatography to obtain desired products with diastereomeric excess of >97%. Ketone 17 thus formed is deprotected using an acid such as HCl in a suitable solvent such as MeOH to provide β-amino ketone 5. Other conditions to remove the t-butylsulfinyl group may be employed as determined by those skilled in the art. Racemic or enantiomerically pure compounds of Formula (I) can thus be prepared from the corresponding racemic or enantiomerically pure β-amino ketone 5 using protocols described for Scheme 1.

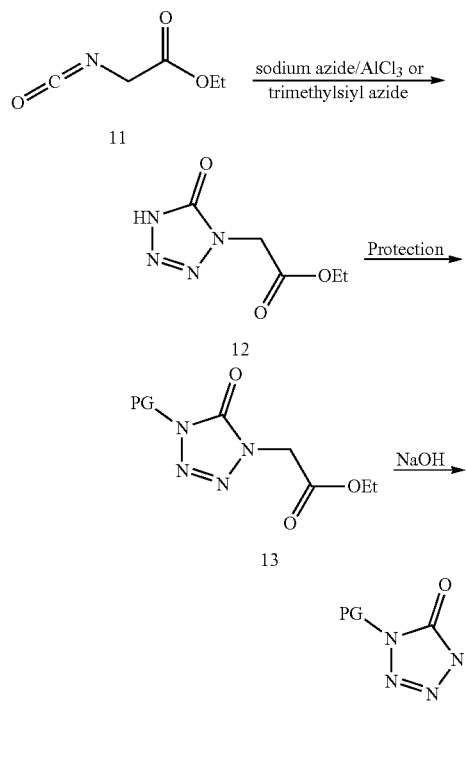

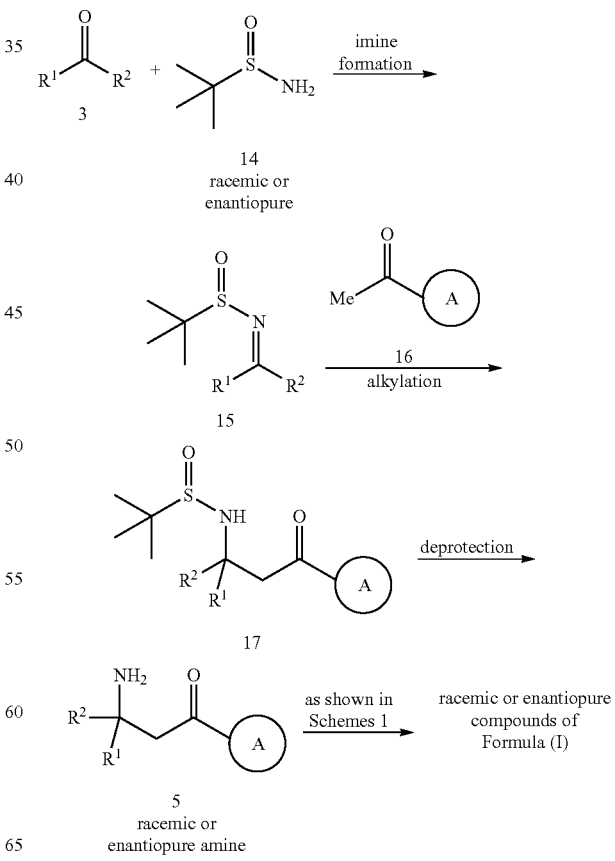

Compounds of Formula (I), where $R^3=R^4=H$, can also be made according to Scheme 4. Ketone 3 is stirred with 2-methylpropane-2-sulfinamide in the presence of a suitable

Scheme 5

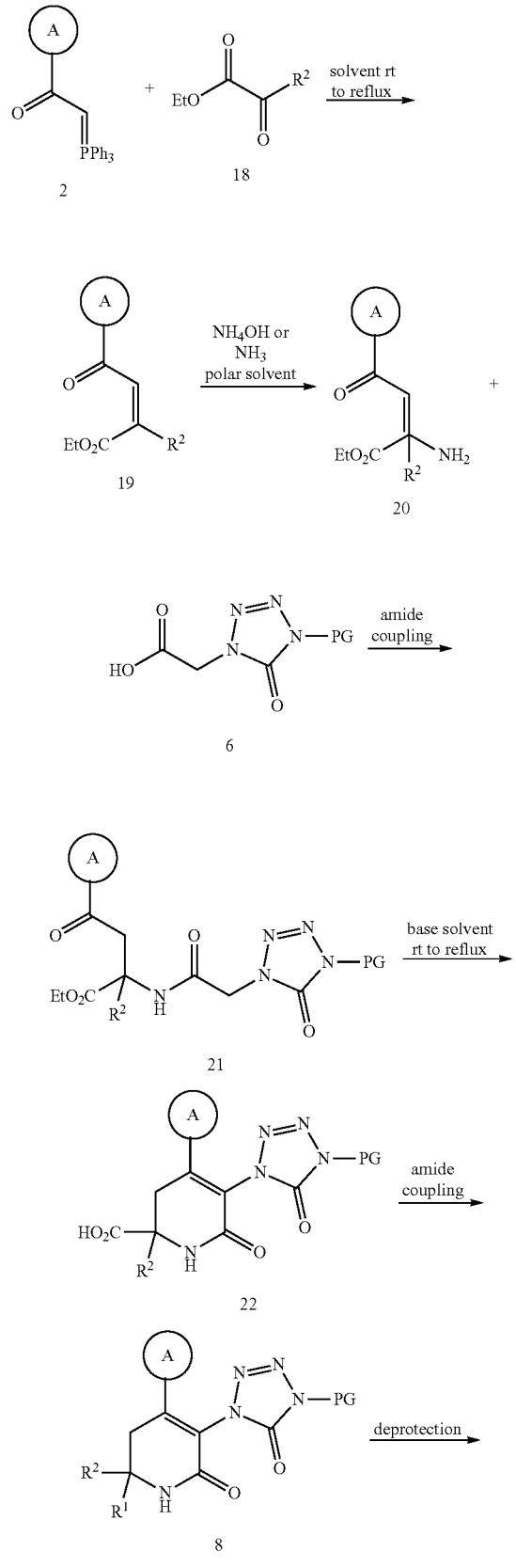

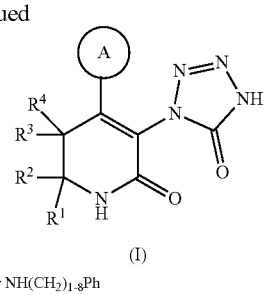

(I)

$R^1$ = CONHC$_{4\text{-}18}$ alkyl, CONHC$_{2\text{-}8}$ haloalkyl or NH(CH$_2$)$_{1\text{-}8}$Ph Compounds of Formula (I), where $R^3$=$R^4$=H and $R^1$=—CONHC$_{4\text{-}18}$ alkyl, —CONHC$_{2\text{-}8}$ haloalkyl or —CONH(CH$_2$)$_{1\text{-}8}$Ph can be made according to Scheme 5. The phosphorous ylide 2 can be heated (ca. 60-80° C.) with a-ketoester 18 in a suitable solvent such as THF or DMSO to give α,β-unsaturated ketone 19. Microwave irradiation may be employed to shorten the reaction time. Treatment of the α,β-unsaturated ketone 19 with concentrated aq NH$_4$OH in a solvent such as DMSO in a sealed vessel can provide amine 20. Alternatively, alkene 19 may be treated with NH$_3$ in a solvent such as DMSO or DMSO and methanol in a sealed vessel to provide amine 20. Amine 20 can be coupled with carboxylic acid 6 as described for Scheme 1 to afford amide 21. Cyclization of amide 21 to afford 22 can occur by stirring 21 in the presence of a weak base such as piperidine in a suitable solvent such as EtOH at a temperature between room temperature and reflux. The resulting cyclized product can be converted to acid 22 by saponification with a base such as lithium hydroxide in a suitable solvent such as THF and water at room temperature. Carboxylic acid 22 and an appropriate amine can be coupled together using standard amide bond forming conditions. For example, treatment of carboxylic acid 22 and the amine with HOBt, EDC and DIEA in the presence of pyridine in a suitable solvent such as DCM at room temperature can provide amide 8. Other amide bond forming reaction known to those skilled in the art may be employed. Compound 8 can be converted to compound of Formula (I) following the protocol described for Scheme 1.

Scheme 6

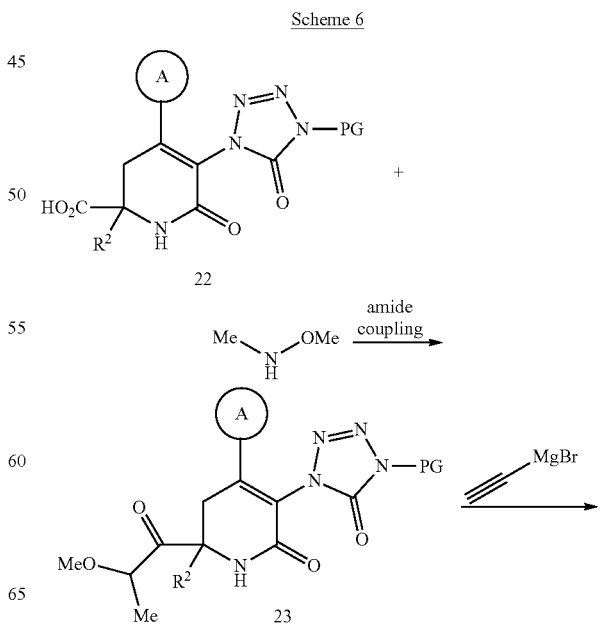

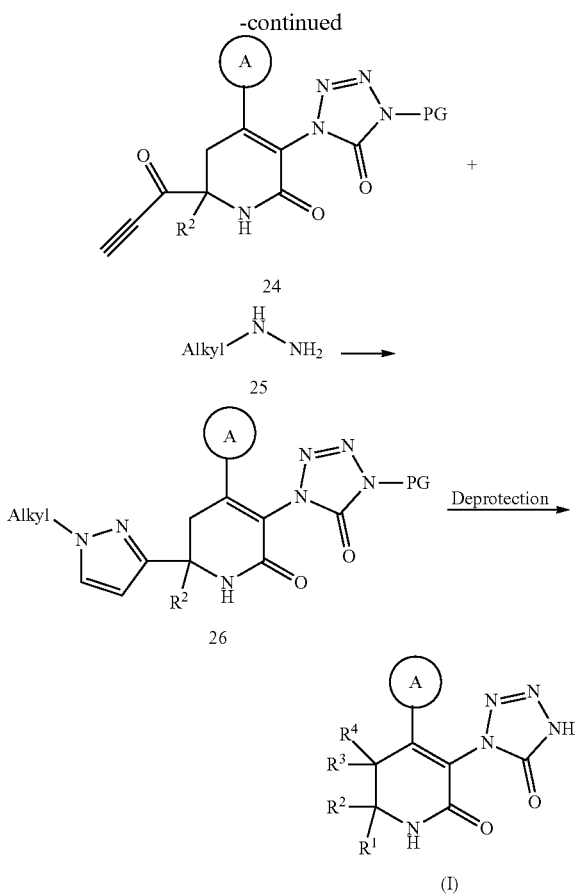

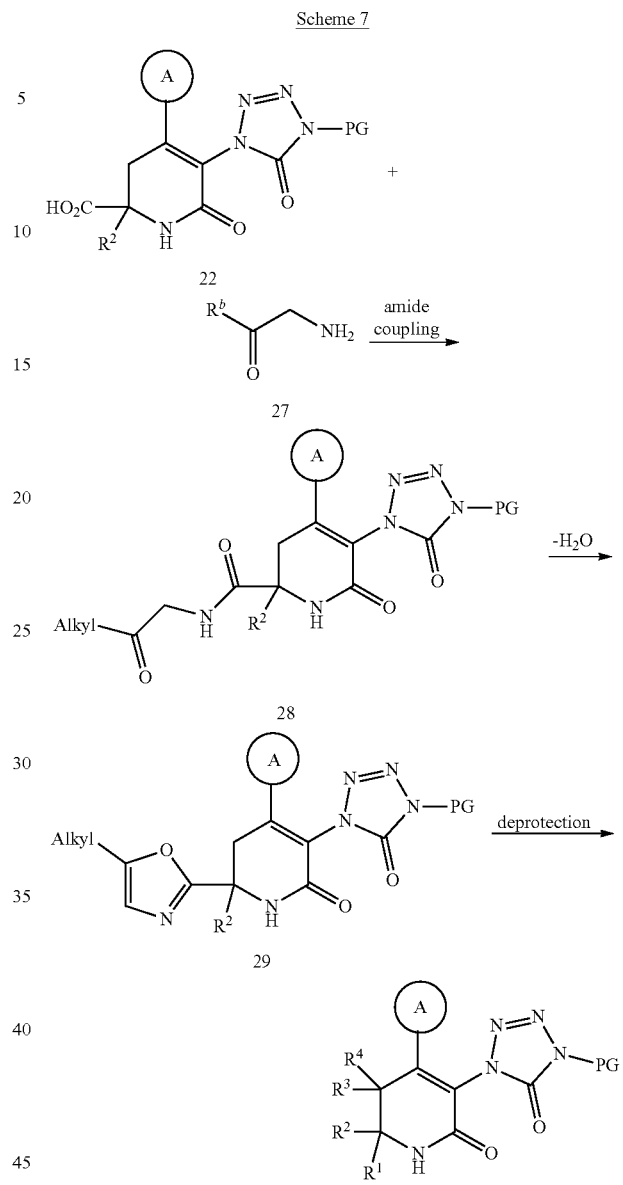

Compounds of formula (I) where $R^1$ is a substituted pyrazole can be prepared as described in Scheme 6. Coupling of acid 22 with N,O-dimethylhydroxylamine using typical amide bond forming reactions (e.g., EDC in the presence of base, preferably N-methylmorpholine, in a suitable solvent, such as dichloromethane) can provide the Weinreb amide 23. Other amide forming reactions known to those skilled in the art may also be employed. The intermediate 23 can be reacted with ethynylmagnesium bromide in an aprotic solvent such as THF at 0-35° C. to provide the acylacetylide intermediate 24. Reaction of 24 with various hydrazines 25 in the presence of a base such as TEA in a suitable solvent such as EtOH can afford pyrazoles 26 which can be transformed to the compounds of Formula (I) as described for Scheme 1.

Compounds of formula (I) where $R^1$ is a substituted oxazole can be prepared as described in Scheme 7. Reaction of 22 with alpha amino ketone 27 using typical amide bond forming reactions (e.g., EDC and HOBt in the presence of base, preferably DIEA, in a suitable solvent, such as dichloromethane) can provide ketoamide 28. Other amide forming reactions known to those skilled in the art may also be employed. The oxazole 29 can be obtained via the dehydrative cyclization using a dehydrating agent, preferably $POCl_3$, in the presence of a suitable base, such as DIEA, in a suitable solvent such as dichloroethane at a temperature of 50-120° C. Compound 29 can be converted to compound of Formula (I) following the protocol described for Scheme 1.

IV. Biology

In mammals, there are two triglyceride synthesis pathways: glycerol-3-phosphate pathway and monoacylglycerol pathway. The former is mainly responsible for energy storage in the peripheral tissues such as fat, liver, skeletal muscle; the latter is essential for the dietary fat absorption which takes place in the small intestine. When dietary fat is ingested, pancreatic lipase digests triglycerides into free fatty acids and 2-monoacylglycerol, which are absorbed by intestinal epithelial enterocytes. Once inside enterocytes, free fatty acids and 2-monoacylglycerol are used as building blocks to resynthesize triglycerides by two sequential acylation steps; first by MGAT and then by DGAT enzyme reactions. Triglycerides are then incorporated into chylomicrons and secreted into lymph to be utilized as an energy supply for the body.

Monoacylglycerol acyltransferase 2 (MGAT2) is a membrane bound acyltransferase that belongs to diacylglycerol acyltransferase 2 (DGAT2) gene family. It is highly and selectively expressed in the small intestine. Genetic deletion of MGAT2 in mice decreased the rate of absorption for the orally ingested triglycerides, indicating that MGAT2 plays an important role for the intestinal MGAT/DGAT pathway [Yen, C. L. et al, Nat. Med., 15(4):442-446 (2009); Okawa, M. et al., Biochem. Biophys. Res. Commun., 390(3):377-381 (2009)]. When chronically challenged with a high fat diet, in contrast to wild type mice that became obese, MGAT2 knockout mice resisted the impact of high-fat feeding and had a lower body weight, less adiposity, and less hepatic fat accumulation. In contrast to hyperinsulinemic wild type mice after high-fat challenge, MGAT2 deletion normalizes the insulin level and decreased fasting glucose. In the glucose tolerance test, they also had an improved glucose excursion. Consistent with their improved glycemic profile, MGAT2 knockout mice also had an increased level of GLP1, an incretin gut hormone that profoundly impacts glucose metabolism [Yen, C. L. et al., Nat. Med., 15(4):442-446 (2009)]. Taken together, it is expected that inhibition of MGAT2 through pharmacological intervention would provide the same benefit as demonstrated in the knock-out mice, e.g., resistance to weight gain, or conversely, reduction in fat body mass. In addition, MGAT2 inhibition would lead to an improved insulin sensitivity and glucose metabolism which either leads to a decrease in the incidence of Type II diabetes, or a treatment of diabetic condition.

It is also desirable and preferable to find compounds with advantageous and improved characteristics compared with known anti-diabetic agents, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood drug concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) improved therapeutic index with less propensity for hypoglycemia.

As used herein, the term "patient" encompasses all mammalian species.

As used herein, the term "subject" refers to any human or non-human organism that could potentially benefit from treatment with a MGAT2 inhibitor. Exemplary subjects include human beings of any age with risk factors for metabolic disease. Common risk factors include, but are not limited to, age, sex, weight, family history, or signs of insulin resistance such as acanthosis nigricans, hypertension, dyslipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; (b) relieving the disease-state, i.e., causing regression of the disease state; and/or (c) preventing the disease-state from occurring in a mammal, in particular, when such mammal is predisposed to the disease-state but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" or "reducing risk" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit MGAT2 and/or to prevent or treat the disorders listed herein. When applied to a combination, the term refers to combined amounts of the active ingredients that result in the preventive or therapeutic effect, whether administered in combination, serially, or simultaneously.

ASSAY METHODS

MGAT LCMS Assay

The MGAT enzyme reactions were performed in Corning FALCON® 96-well polypropylene plates, in a total volume of 60 µL of 50 mM potassium phosphate buffer pH 7.4, containing a final concentration of 100 µM 2-oleoylglycerol, 15 µM oleoyl-coenzyme A and 0.0013 µg/µL human or mouse MGAT-2 or 0.0026 µg/µL rat recombinant MGAT-2 membranes expressed in Sf9 cells. Assay plates were run through a fully automated robotics system and shaken for 5 seconds every minute for a total 10 minutes. The reactions were then quenched with 120 µL of ice cold methanol containing 1 µg/mL 1,2-distearoyl-rac-glycerol as the internal standard. Plates were shaken for 2 minutes and spun down to remove protein precipitation. After the spin, samples were transferred to LC/MS compatible PCR plates. For LC/MS analysis, a ThermoFisher Surveyor pump, utilizing a Waters SYMMETRY® C8, 50×2.1 mm column, was used for the chromatography of enzyme products. The buffer system consists of 0.1% formic acid in water with a mobile phase consisting 0.1% formic acid in methanol. The shallow gradient is 90-100% mobile phase in 0.2 min with a total run time of 2.3 min. The first 0.5 minutes of each injection was diverted to waste to eliminate the presence of Phosphate buffer in the enzymatic reaction. The column was run at 0.6 mL/min and a temperature of 65° C. Mass spectrometry analysis of the samples was performed on a ThermoFisher Quantum Triple quad utilizing APCI (+) as the mode of ionization. Data was acquired in Single Ion Monitoring (SIM) mode analyzing Diolein=m/z 603.6 (PRODUCT) and 1,2-distearoyl-rac-glycerol (IS)=m/z 607.6. The ratio of Diolein to internal standard (Peak Area Ratio) is utilized to calculate $IC_{50}$ values.

The exemplified Examples disclosed below were tested in the MGAT2 in vitro assays described above and were found having MGAT2 inhibitory activity. Table 1 below lists human MGAT2 $IC_{50}$ values measured for the following examples.

TABLE 1

| Example No. | h-MGAT LCMS $IC_{50}$ (nM) |
| --- | --- |
| 1 | 27 |
| 2 | 5 |
| 3 | 340 |

TABLE 1-continued

| Example No. | h-MGAT LCMS $IC_{50}$ (nM) |
|---|---|
| 4 | 17 |
| 5 | 71 |
| 6 | 137 |
| 7 | 173 |
| 8 | 30 |
| 9 | 108 |
| 10 | 36 |
| 11 | 9 |
| 12 | 34 |
| 13 | 84 |
| 14 | 5 |
| 15 | 145 |
| 16 | 5 |
| 17 | 5 |
| 18 | 8 |
| 19 | 10 |
| 20 | 3 |
| 21 | 10 |
| 22 | 2 |
| 23 | 60 |
| 24 | 36 |

The compounds of the present invention possess activity as inhibitors of MGAT2, and, therefore, may be used in the treatment of diseases associated with MGAT2 activity. Via modulation of MGAT2, the compounds of the present invention may preferably be employed to modulate, either enhance or decrease the production/secretion of insulin and/or gut hormones, such as GLP1, GIP, CCK, PYY, PP, Amylin.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, gestational diabetes, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, dyslipidemia, hyperlipidemia, hypertriglyceridemia, hypercholesterolemia, low HDL, high LDL, lipid disorders, PCOS, and glaucoma.

Metabolic Syndrome or "Syndrome X" is described in Ford et al., *J. Am. Med. Assoc.*, 287:356-359 (2002) and Arbeeny et al., *Curr. Med. Chem.-Imm., Endoc. & Metab. Agents*, 1:1-24 (2001).

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; buccally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anti-diabetic agent or other pharmaceutically active material.

The compounds of the present invention may be employed in combination with other MGAT2 inhibitors or one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, or cognition promoting agents, appetite suppressants, treatments for heart failure, treatments for peripheral arterial disease and anti-inflammatory agents.

Where desired, the compound of the present invention may be used in combination with one or more other types of anti-diabetic agents and/or one or more other types of therapeutic agents which may be administered orally in the same dosage form, in a separate oral dosage form or by injection. The other type of anti-diabetic agent that may be optionally employed in combination with the MGAT2 inhibitor of the present invention may be one, two, three or more anti-diabetic agents or antihyperglycemic agents which may be administered orally in the same dosage form, in a separate oral dosage form, or by injection to produce an additional pharmacological benefit.

The anti-diabetic agents used in the combination with the compound of the present invention include, but are not limited to, insulin secretagogues or insulin sensitizers, other MGAT2 inhibitors, or other anti-diabetic agents. These agents include, but are not limited to, dipeptidyl peptidase IV (DP4) inhibitors (for example, sitagliptin, saxagliptin, alogliptin, vildagliptin and the like), biguanides (for example, metformin, phenformin and the like), sulfonyl ureas (for example, glyburide, glimepiride, glipizide and the like), glucosidase inhibitors (for example, acarbose, miglitol, and the like), PPARγ agonists such as thiazolidinediones (for example, rosiglitazone, pioglitazone, and the like), PPAR α/γ dual agonists (for example, muraglitazar, tesaglitazar, aleglitazar, and the like), glucokinase activators (as described in Fyfe, M. C. T. et al., *Drugs of the Future*, 34(8):641-653 (2009) and incorporated herein by reference), GPR40 receptor modulators, GPR119 receptor modulators (MBX-2952, PSN821, APD597 and the like), SGLT2 inhibitors (dapagliflozin, canagliflozin, remagliflozin and the like), amylin analogs such as pramlintide, and/or insulin. Reviews of current and emerging therapies for the treatment of diabetes can be found in: Mohler, M. L. et al., *Medicinal Research Reviews*, 29(1):125-195 (2009), and Mizuno, C. S. et al., *Current Medicinal Chemistry*, 15:61-74 (2008).

The compounds of the present invention may also be optionally employed in combination with agents for treating complication of diabetes. These agents include PKC inhibitors and/or AGE inhibitors.

The compounds of the present invention may also be optionally employed in combination with one or more hypophagic agents such as diethylpropion, phendimetrazine, phentermine, orlistat, sibutramine, lorcaserin, pramlintide, topiramate, MCHR1 receptor antagonists, oxyntomodulin, naltrexone, Amylin peptide, NPY Y5 receptor modulators, NPY Y2 receptor modulators, NPY Y4 receptor modulators, cetilistat, 5HT2c receptor modulators, and the like. The compound of structure I may also be employed in combination with an agonist of the glucagon-like peptide-1 receptor (GLP-1 R), such as exenatide, liraglutide, GPR-1(1-36) amide, GLP-1(7-36) amide, GLP-1(7-37) (as disclosed in U.S. Pat. No. 5,614,492 to Habener, the disclosure of which is incorporated herein by reference), which may be administered via injection, intranasal, or by transdermal or buccal devices. Reviews of current and emerging therapies for the treatment of obesity can be found in: Melnikova, I. et al., *Nature Reviews Drug Discovery*, 5:369-370 (2006); Jones, D., *Nature Reviews: Drug Discovery*, 8:833-834 (2009); Obici, S., *Endocrinology*, 150(6):2512-2517 (2009); and Elangbam, C. S., *Vet. Pathol.*, 46(1):10-24 (2009).

The compounds of the present invention may also be optionally employed in combination with one or more other types of therapeutic agents, such as DGAT inhibitors, LDL lowering drugs such as statins (inhibitors of HMG CoA reductase) or inhibitors of cholesterol absorption, modulators of PCSK9, drugs increase HDL such as CETP inhibitors.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the MGAT2 enzyme. Such compounds may be provided in a commercial kit, for example, for use in pharmaceutical research involving MGAT2 or anti-diabetic activity. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving MGAT2.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment and/or prophylaxis of multiple diseases or disorders associated with MGAT2 (as defined previously). In another embodiment, the package insert states that the pharmaceutical composition can be used in combination (as defined previously) with a second therapeutic agent for the treatment and/or prophylaxis of multiple diseases or disorders associated with MGAT2. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof.

VI. EXAMPLES

The following Examples are offered as illustrative, as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

HPLC/MS, Preparatory/Analytical HPLC, and Chiral Separation Methods Employed in Characterization or Purification of Examples Analytical HPLC/MS (unless otherwise noted) was performed on Shimadzu SCL-10A liquid chromatographs and Waters MICROMASS® ZQ Mass Spectrometers (Desolvation Gas: Nitrogen; Desolvation Temp. 250° C.; Ion Source Temp: 120° C.; Positive Electrospray conditions) using the following methods:

Linear Gradient of 0% to 100% Solvent B over 2 min, with 1 minute hold at 100% B, or Linear Gradient of 0% to 100% Solvent B over 4 min, with 1 minute hold at 100% B;

UV visualization at 220 nm;
Column: PHENOMENEX® Luna C18 (2) 30 mm×4.6 mm; 5µparticle (heated to Temp. 40° C.);
Flow rate: 1.0 mL/min (2 min gradient) or 0.8 ml/min (4 min gradient);
Solvent A: 10% ACN, 90% water, 0.1% TFA; or, 10% MeOH, 90% water, 0.1% TFA; and
Solvent B: 90% ACN, 10% water, 0.1% TFA; or, 90% MeOH, 10% water, 0.1% TFA.
Preparatory HPLC (unless otherwise noted) was performed on a Shimadzu SCL-10A liquid chromatograph with a linear gradient of 20-100% Solvent B over 10 to 30 min, with either a 2 to 5 min hold at 100% Solvent B as determined by on skilled in the art;
UV visualization at 220 nm;
Column: PHENOMENEX® Luna Axia 5p C18 30×100 mm;
Flow rate: 20 mL/min;
Solvent A: 10% ACN, 90% water, 0.1% TFA; or 10% MeOH, 90% water, 0.1% TFA; and
Solvent B: 90% ACN, 10% water, 0.1% TFA; or 90% MeOH, 10% water, 0.1% TFA.

NMR Employed in Characterization of Examples $^1$H NMR spectra (unless otherwise noted) were obtained with JEOL® or Bruker Fourier transform spectrometers operating at 400 MHz or 500 MHz. $^1$H-nOe experiments were performed in some cases for regiochemistry elucidation with a 400 MHz Bruker Fourier Transform spectrometer.

Spectral data are reported as chemical shift (multiplicity, number of hydrogens, coupling constants in Hz) and are reported in ppm (δ units) relative to either an internal standard (tetramethyl silane=0 ppm) for $^1$H NMR spectra, or are referenced to the residual solvent peak (2.49 ppm for $CD_3SOCD_2H$, 3.30 ppm for $CD_2HOD$, 1.94 for $CHD_2CN$, 7.26 ppm for $CHCl_3$, 5.32 ppm for $CDHCl_2$).

Microwave instrumentation employed in heating reactions.

BIOTAGE® Initiator 2.5, maximum power 400 W, reaction volume range 0.2-10 mL. Reactions are run in sealed pressure vessels specially manufactured for this instrument.

Intermediate 1

2-(4-(4-Methoxybenzyl)-5-oxo-4,5-dihydro-1H-tetrazol-1-yl)acetic acid

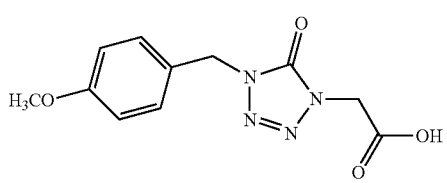 [SMILES: COc1ccc(Cn2nnn(CC(=O)O)c2=O)cc1]

Intermediate 1A. Ethyl 2-(5-oxo-4,5-dihydro-1H-tetrazol-1-yl)acetate: A solution of aluminium chloride (0.568 g, 4.26 mmol) in THF (3 mL) was added dropwise to a stirred mixture of ethyl isocyanatoacetate (0.5 g, 3.87 mmol) and sodium azide (0.579 g, 8.91 mmol) in THF (10 mL) and stirred at reflux for 21 h (US 2010/0016365 A1). The reaction mixture was cooled to rt and acidified to pH ~3 using 4N HCl. The mixture was diluted with EtOAc and MeOH, filtered, and the filtrate was concentrated. The crude product was purified using ISCO flash chromatography (silica gel/DCM:MeOH 100:0 to 80:20 gradient) to afford 1A (179 mg, 27%) as a yellow oil (solidified upon standing at rt).

Alternatively, Intermediate 1A can be prepared as follows: Azidotrimethylsilane (4.1 g, 35.6 mmol) and ethyl isocyanatoacetate (2.0 g, 15.49 mmol) were charged to a sealed tube that was equipped with a magnetic stirrer and the reaction mixture was stirred at 95° C. for 18 h. The reaction was cooled to rt and concentrated in vacuo to a clear oil that was purified using ISCO flash chromatography as above to afford Intermediate 1A (1.82 g, 68.2%) as a white solid. MS (m/z) [M+H]$^+$ 173.

Intermediate 1B. Ethyl 2-(4-(4-methoxybenzyl)-5-oxo-4,5-dihydro-1H-tetrazol-1-yl)acetate: A mixture of Intermediate 1A (2.386 g, 13.86 mmol), 1-(chloromethyl)-4-methoxybenzene (2.82 g, 18.02 mmol), and potassium carbonate (3.83 g, 27.7 mmol) in acetonitrile (75 mL) was stirred at 70° C. for 20 h. The reaction was cooled to rt, filtered, and concentrated. The crude product was purified using ISCO flash chromatography (silica gel/EtOAc-hexanes 0:100 to 50:50 gradient) to afford Intermediate 1B (2.66 g, 66%). MS (m/z) [M+H]$^+$ 293.

Intermediate 1: A mixture of Intermediate 1B (2.66 g, 9.11 mmol) and IN NaOH (27.3 mL, 27.3 mmol) in THF (200 mL) was stirred at rt for 2 h. The reaction mixture was concentrated in vacuo to a yellow solid that was dissolved in EtOAc (50 mL) and acidified using IN HCl. The phases were split and the organic phase was dried ($MgSO_4$), and concentrated to afford Intermediate 1 as a pale yellow solid. MS (m/z) [M+H]$^+$ 265. $^1$H NMR (400 MHz, chloroform-d) δ 7.31 (d, J=8.8 Hz, 2H), 6.88 (d, J=8.53 Hz, 2H), 5.06 (s, 2H), 4.76 (s, 2H), 3.79 (s, 3H).

Intermediate 2

(S)-3-Amino-4,4,4-trifluoro-1-(p-tolyl)-3-(4-(4,4,4-trifluorobutoxy)phenyl)butan-1-one

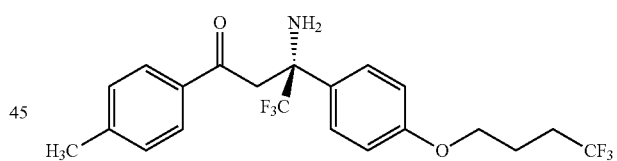

Intermediate 2A. 4-(4,4,4-Trifluorobutoxy)benzaldehyde: To a solution of 4-hydroxybenzaldehyde (20 g, 164 mmol) and 4,4,4-trifluorobutan-1-ol (25 g, 195 mmol) in anhydrous $CH_2Cl_2$ (500 mL) at 0° C. under Ar was added a solution of $PPh_3$ (51.5 g, 196 mmol) in $CH_2Cl_2$ (200 mL) over 15 min, followed by dropwise addition of a solution of DIAD (36.4 g, 180 mmol) in anhydrous $CH_2Cl_2$ (150 mL). The mixture was stirred at 0° C. for 0.5 h. The reaction was warmed to rt and stirred for another 3 h. The solvent was removed in vacuo and the residue was triturated with $CH_2Cl_2$ three times to remove insoluble solids. The combined $CH_2Cl_2$ washings were concentrated and the residue was purified by silica gel chromatography (330 g silica gel, eluted with EtOAc in hexanes) to provide Intermediate 2A (27 g, 71%) as a light brown oil. MS (m/z) [M+H]$^+$ 233.

Intermediate 2B. 2,2,2-Trifluoro-1-(4-(4,4,4-trifluorobutoxy)phenyl)ethanol: To a solution of Intermediate 2A (26.7 g, 114 mmol) and trimethyl(trifluoromethyl)silane (16.9 g, 119 mmol) in anhydrous DME (112 mL) was added CsF (500 mg, 3.29 mmol). The reaction was stirred at rt for 16 h. To the mixture was added 4N aq HCl (114 mL) and the mixture was stirred at rt for 2.5 h. The reaction was diluted with EtOAc (300 mL) and sequentially washed with water, saturated aqueous NaHCO₃ and brine. The organic phase was dried over anhydrous MgSO₄, filtered and concentrated to provide Intermediate 2B (42.5 g, 122%) as an oil. The crude product was used without further purification. MS (m/z) [M−H] 301.

Intermediate 2C. 2,2,2-Trifluoro-1-(4-(4,4,4-trifluorobutoxy)phenyl)ethanone: To a solution of Intermediate 2B (115 mmol) in anhydrous CH₂Cl₂ (320 mL) was added Dess-Martin periodinane (50.2 g, 118 mmol) portionwise at 0° C. The reaction was stirred at 0° C. for 0.5 h then at rt for 3 h. To the reaction was added 100 mL of saturated aq Na₂CO₃ and 250 mL of EtOAc. The reaction was stirred for another 2 h. The insoluble material was removed by filtration. The layers were separated. The organic layer was washed with saturated aq Na₂CO₃. Additional solids that formed upon standing overnight were removed. The organic solution was washed with saturated aq NaCl, dried over anhydrous MgSO₄, filtered and concentrated to provide a dark brown liquid. This material was purified by silica gel chromatography (220 g silica gel, eluted with EtOAc in hexanes to provide Intermediate 2C (26 g, 76%) as a colorless oil.

Intermediate 2D. (S,E)-2-Methyl-N-(2,2,2-trifluoro-1-(4-(4,4,4-trifluorobutoxy)phenyl)ethylidene)propane-2-sulfinamide: To a solution of Intermediate 2C (10 g, 33.3 mmol) and (S)-2-methylpropane-2-sulfinamide (8.07 g, 66.6 mmol) in THF (125 mL) was added a solution of tetraisopropoxytitanium (37.9 g, 133 mmol) in THF (45 mL) and the reaction mixture was stirred at 65° C. for 4 h. The reaction solvent was removed under vacuum, the residue was dissolved in EtOAc (200 mL) and the solution was washed with sat. aq NaHCO₃ (150 mL). A large amount of solids formed that were removed by filtration through CELITE®. The solid was washed with EtOAc (2×140 mL). The combined filtrate was washed with sat. aq NaHCO₃ (100 mL), dried over MgSO₄ and concentrated in vacuo to afford a yellow oil that purified by chromatography (silica ge/hexanes-EtOAc gradient) to give the desired imine Intermediate 2D as a yellow oil (9.64 g, 71.7%).

Intermediate 2E. 2-Methyl-N—((S)-1,1,1-trifluoro-4-oxo-4-(p-tolyl)-2-(4-(4,4,4-trifluorobutoxy)phenyl)butan-2-yl)propane-2-sulfinamide: Potassium bis(trimethylsilyl)amide (0.709 mL, 0.709 mmol) was added at −78° C. to a solution of 1-(p-tolyl)ethanone (0.130 g, 0.967 mmol) in ether (2 mL) and stirred for 5 min. Then, a solution of 2D (0.26 g, 0.645 mmol) in ether (2 mL) was added and stirred at −78° C. for 1 h. The mixture was quenched with MeOH, diluted with DCM, washed with water, dried (MgSO₄), and concentrated. The crude was purified using ISCO flash chromatography (silica gel/hexanes-ethyl acetate 100:0 to 50:50 gradient) to give Intermediate 2E (0.24 g, 0.448 mmol, 70% yield) as a colorless oil.

Intermediate 2. (S)-3-Amino-4,4,4-trifluoro-1-(p-tolyl)-3-(4-(4,4,4-trifluorobutoxy)phenyl)butan-1-one: A solution of Intermediate 2E (0.24 g, 0.446 mmol) and 5N HCl in isopropyl alcohol (1.5 mL, 7.50 mmol) in MeOH (2 mL) was stirred at rt for 40 min. The mixture was concentrated, diluted with DCM, washed with sat. NaHCO₃, dried (MgSO₄), and concentrated to give Intermediate 2 (0.179 g, 0.413 mmol, 93% yield) as a colorless oil.

Example 1

(S)-3-(5-Oxo-4,5-dihydro-1H-tetrazol-1-yl)-4-(p-tolyl)-6-(4-(4,4,4-trifluorobutoxy)phenyl)-6-(trifluoromethyl)-5,6-dihydropyridin-2(1H)-one

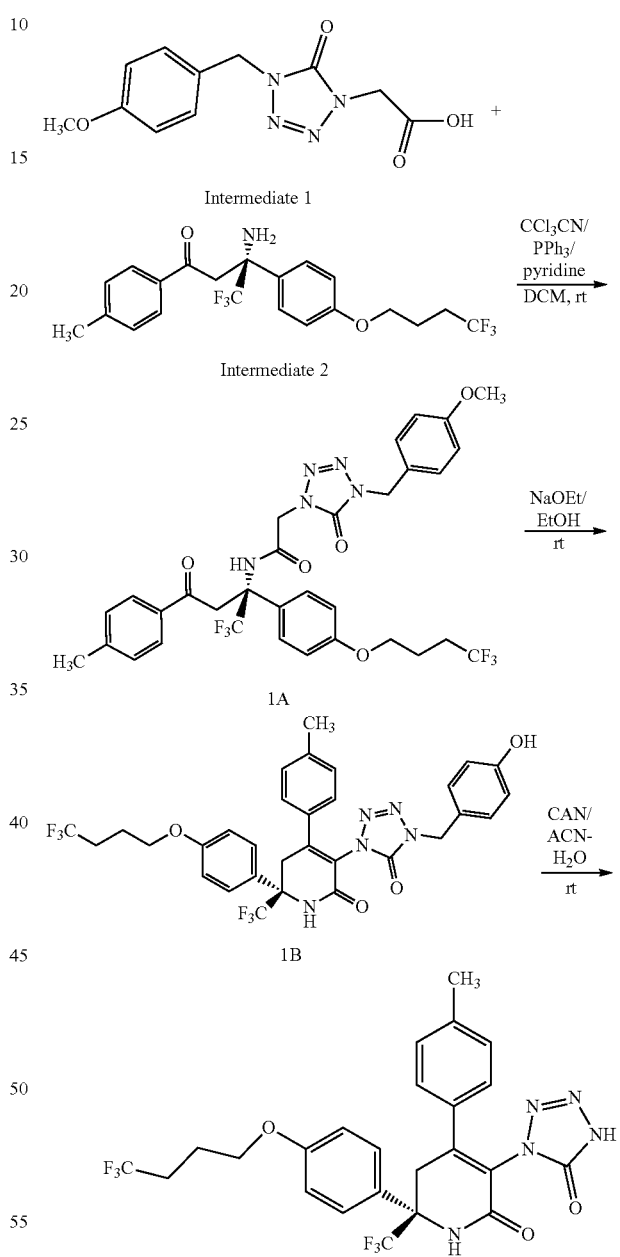

Example 1

1A. (S)-2-(4-(4-Methoxybenzyl)-5-oxo-4,5-dihydro-1H-tetrazol-1-yl)-N-(1,1,1-trifluoro-4-oxo-4-(p-tolyl)-2-(4-(4,4,4-trifluorobutoxy)phenyl)butan-2-yl)acetamide: Trichloroacetonitrile (0.02 mL, 0.17 mmol) was added dropwise to a solution of Intermediate 1 (20 mg, 0.08 mmol) and triphenylphosphine (76 mg, 0.29 mmol) in DCM (1.5 mL) and stirred at rt for 1.5 h. Then, a solution of Intermediate 2 (25 mg, 0.06 mmol) in DCM (0.5 mL) followed by pyridine (0.014 mL, 0.17 mmol) were added. The reaction mixture was stirred at rt overnight, concentrated, and the crude product was purified using prep HPLC (C18 column/10:90: 0.1 to 90:10:0.1 ACN —H₂O-TFA gradient) to afford 1A (16 mg, 40.8%). MS (m/z) [M+H]⁺ 680.

1B. (S)-3-(4-(4-Methoxybenzyl)-5-oxo-4,5-dihydro-1H-tetrazol-1-yl)-4-(p-tolyl)-6-(4-(4,4,4-trifluorobutoxy)phenyl)-6-(trifluoromethyl)-5,6-dihydropyridin-2(1H)-one: Sodium ethoxide (0.03 mL, 0.07 mmol) was added to a solution of 1A (16 mg, 0.02 mmol) in EtOH (0.6 mL) and stirred at rt for 2 h. The mixture was diluted with DCM, washed with 1N HCl, dried (MgSO₄), and concentrated to afford crude 1B (13.5 mg, 87%). MS (m/z) [M+H]⁺ 662.

Example 1. (S)-3-(5-Oxo-4,5-dihydro-1H-tetrazol-1-yl)-4-(p-tolyl)-6-(4-(4,4,4-trifluorobutoxy)phenyl)-6-(trifluoromethyl)-5,6-dihydropyridin-2(1H)-one: A solution of 1B (8 mg, 0.012 mmol) and ceric ammonium nitrate (66.3 mg, 0.12 mmol) in acetonitrile (0.5 mL) and water (0.2 mL) was stirred at rt for 3 h, diluted with EtOAc, washed with water, dried (MgSO₄), and concentrated. The crude product was purified using prep HPLC (C18 column/10:90:0.1 to 90:10: 0.1 MeOH—H₂O-TFA gradient) to afford Example 1 (5.3 mg, 79%) as a white solid. MS (m/z) [M+H]⁺ 542. ¹H NMR (400 MHz, chloroform-d) δ 7.48 (d, J=8.6 Hz, 2H), 7.16 (d, J=7.9 Hz, 2H), 7.06 (d, J=7.9 Hz, 2H), 6.97 (d, J=8.9 Hz, 2H), 4.06 (t, J=5.9 Hz, 2H), 3.80 (br. s., 1H), 3.54 (d, J=17.6 Hz, 1H), 2.39-2.28 (m, 5H), 2.14-2.04 (m, 2H).

The following Examples in Table 2 were prepared in a similar manner as Example 1.

TABLE 2

| Example | Structure and Name | Analytical Data |
| --- | --- | --- |
| 2 | 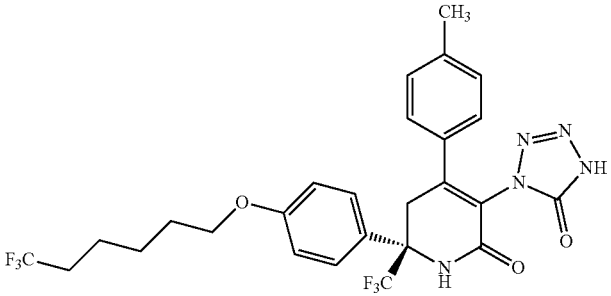<br>(S)-3-(5-oxo-4,5-dihydro-1H-tetrazol-1-yl)-4-(p-tolyl)-6-(4-((6,6,6-trifluorohexyl)oxy)phenyl)-6-(trifluoromethyl)-5,6-dihydropyridin-2(1H)-one | ¹H NMR (400 MHz, chloroform-d) δ 7.46 (d, J = 7.1 Hz, 2H), 7.15 (d, J = 7.6 Hz, 2H), 7.10-7.02 (m, 2H), 6.96 (d, J = 8.8 Hz, 2H), 4.01 (t, J = 6.2 Hz, 2H), 3.80 (d, J = 16.4 Hz, 1H), 3.52 (d, J = 17.6 Hz, 1H), 2.34 (s, 3H), 2.22-2.05 (m, 2H), 1.84 (quin, J = 6.7 Hz, 2H), 1.72-1.55 (m, 4H). MS (ESI) m/z: 570.4 (M + H)⁺. |
| 3 | 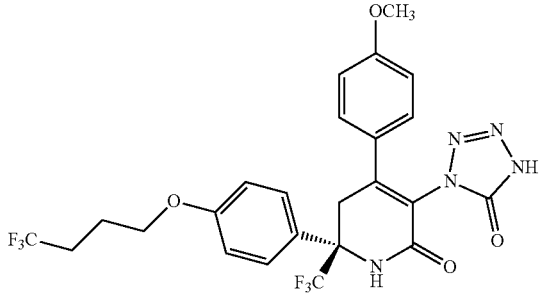<br>(S)-4-(4-methoxyphenyl)-3-(5-oxo-4,5-dihydro-1H-tetrazol-1-yl)-6-(4-((4,4,4-trifluorobutoxy)phenyl)-6-(trifluoromethyl)-5,6-dihydropyridin-2(1H)-one | ¹H NMR (400 MHz, chloroform-d) δ 7.46 (d, J = 8.4 Hz, 2H), 7.16-7.10 (m, 2H), 6.98-6.93 (m, 2H), 6.88-6.82 (m, 2H), 6.77-6.62 (m, 1H), 4.04 (t, J = 5.8 Hz, 2H), 3.89-3.70 (m, 4H), 3.52 (d, J = 17.2 Hz, 1H), 2.39-2.25 (m, 2H), 2.13-2.02 (m, 2H). MS (ESI) m/z: 558.4 (M + H)⁺. |
| 4 | 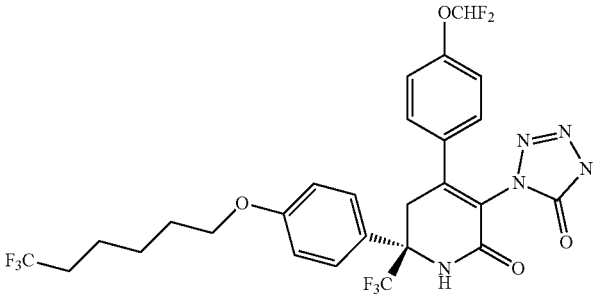<br>(S)-4-(4-difluoromethoxy)phenyl)-3-(5-oxo-4,5-dihydro-1H-tetrazol-1-yl)-6-(4-((6,6,6-trifluorohexyl)oxy)phenyl)-6-(trifluoromethyl)-5,6-dihydropyridin-2(1H)-one | ¹H NMR (400 MHz, chloroform-d) δ 7.45 (d, J = 8.4 Hz, 2H), 7.19 (d, J = 8.6 Hz, 2H), 7.13-7.06 (m, 2H), 6.97 (d, J = 8.8 Hz, 2H), 6.49 (br. s., 1H), 6.52 (t, J = 73.7 Hz, 1H), 4.00 (t, J = 6.3 Hz, 2H), 3.77 (br. s., 1H), 3.50 (d, J = 17.6 Hz, 1H), 2.22-2.05 (m, 2H), 1.89-1.79 (m, 2H), 1.77-1.51 (m, 4H). MS (ESI) m/z: 622.4 (M + H)⁺. |

TABLE 2-continued

| Example | Structure and Name | Analytical Data |
|---|---|---|
| 5 | 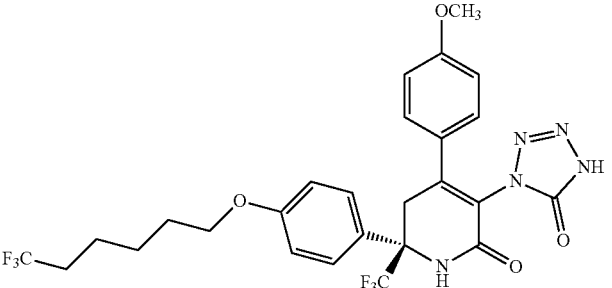<br>(S)-4-(4-methoxyphenyl)-3-(5-oxo-4,5-dihydro-1H-tetrazol-1-yl)-6-(4-(((6,6,6-trifluorohexyl)oxy)phenyl)-6-(trifluoromethyl)-5,6-dihydropyridin-2(1H)-one | $^1$H NMR (500 MHz, DMSO-$d_6$) δ 7.58 (d, J = 8.8 Hz, 2H), 7.20 (d, J = 8.4 Hz, 2H), 7.01-6.88 (m, 4H), 3.99 (t, J = 5.9 Hz, 2H), 3.92-3.77 (m, 1H), 3.75 (s, 3H), 3.73-3.61 (m, 1H), 2.32-2.19 (m, 2H), 1.78-1.69 (m, 2H), 1.59-1.44 (m, J = 13.8, 7.2, 7.2 Hz, 4H). MS (ESI) m/z: 586.2 (M + H)$^+$. |
| 6 | 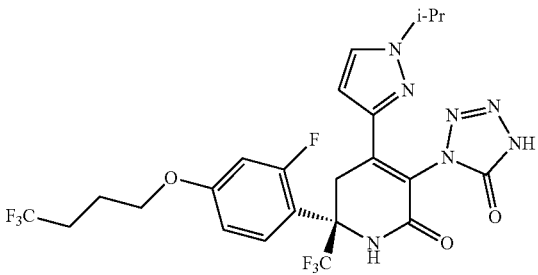<br>(S)-6-(2-fluoro-4-(4,4,4-trifluorobutoxy)phenyl)-4-(1-isopropyl-1H-pyrazol-3-yl)-3-(5-oxo-4,5-dihydro-1H-tetrazol-1-yl)-6-(trifluoromethyl)-5,6-dihydropyridin-2(1H)-one | $^1$H NMR (500 MHz, DMSO-$d_6$) δ 7.85 (br. S., 1H), 7.59-7.49 (m, 1H), 6.90 (d, J = 13.1 Hz, 2H), 6.24-6.02 (m, 1H), 4.57-4.42 (m, 1H), 4.28 (t, J = 15.6 Hz, 1H), 4.11-4.02 (m 2H), 3.79-3.61 (m, 1H), 2.45-2.33 (m, 2H), 2.0-1.88 (m., 2H), 1.47-1.25 (m, 6H). MS (ESI) m/z: 578.3 (M + H)$^+$. |
| 7 | 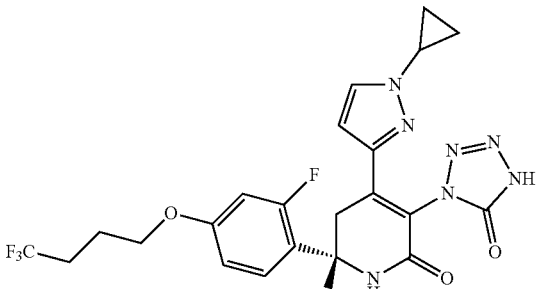<br>(S)-4-(1-cyclopropyl-1H-pyrazol-3-yl)-6-(2-fluoro-4-(4,4,4-trifluorobutoxy)phenyl)-3-(5-oxo-4,5-dihydro-1H-tetrazol-1-yl)-6-(trifluoromethyl)-5,6-dihydropyridin-2(1H)-one | $^1$H NMR (500 MHz, DMSO-$d_6$) δ 7.91 (br. s., 1H), 7.66-7.50 (m, 1H), 7.03-6.85 (m, 2H), 6.01 (d, J = 16.8 Hz, 1H), 4.40-4.22 (m, 1H), 4.12 (t, J = 6.0 Hz, 2H), 4.00-3.60 (m, 2H), 2.52-2.38 (m, 2H), 2.04-1.92 (m 2H), 1.09-0.98 (m, 4H). MS (ESI) m/z: 576.3 (M + H)$^+$. |

TABLE 2-continued

| Example | Structure and Name | Analytical Data |
| --- | --- | --- |
| 8 | 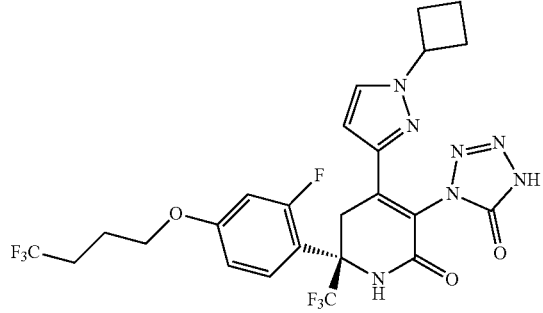<br>(S)-4-(1-cyclopropyl-1H-pyrazol-3-yl)-6-(2-fluoro-4-(4,4,4-trifluorobutoxy)phenyl)-3-(5-oxo-4,5-dihydro-1H-tetrazol-1-yl)-6-(trifluoromethyl)-5,6-dihydropyridin-2(1H)-one | $^1$H NMR (500 MHz, DMSO-$d_6$) δ 7.78 (br. s., 1H), 7.51-7.41 (m, 1H), 6.88-6.76 (m, 2H), 6.02 (d, J = 28.1 Hz, 1H), 5.99 (br. s., 1H), 4.83-4.71 (m, 1H), 4.28-4.12 (m, 1H), 4.00 (t, J = 5.5 Hz, 2H), 3.71-3.52 (m, 1H), 2.38-2.23 (m, 6H), 1.901-1.80 (m 2H), 1.78-1.65 (m, 2H). MS (ESI) m/z: 590.3 (M + H)$^+$. |
| 9 | 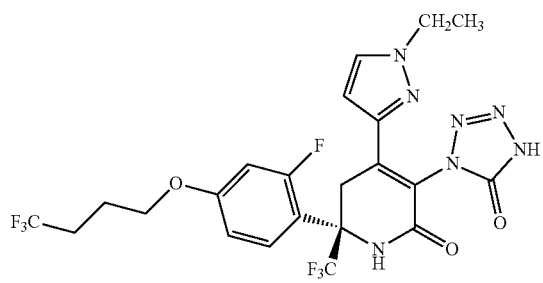<br>(S)-4-(1-ethyl-1H-pyrazol-3-yl)-6-(2-fluoro-4-(4,4,4-trifluorobutoxy)phenyl)-3-(5-oxo-4,5-dihydro-1H-tetrazol-1-yl)-6-(trifluoromethyl)-5,6-dihydropyridin-2(1H)-one | $^1$H NMR (500 MHz, DMSO-$d_6$) δ 7.81 (br. S., 1H), 7.58-7.48 (m, 1H), 6.97-6.80 (m, 2H), 5.97 (d, J = 27.5 Hz, 1H), 4.34-4.22 (m, 1H), 4.15 (q, J = 6.7 Hz, 2H), 4.06 (t, J = 5.5 Hz, 2H), 3.79-3.61 (m, 1H), 2.45-2.32 (m, 2H), 1.98-1.88 (m., 2H), 1.34 (t, J = 6.0 Hz, 3H). MS (ESI) m/z: 564.2 (M + H)$^+$. |
| 10 | 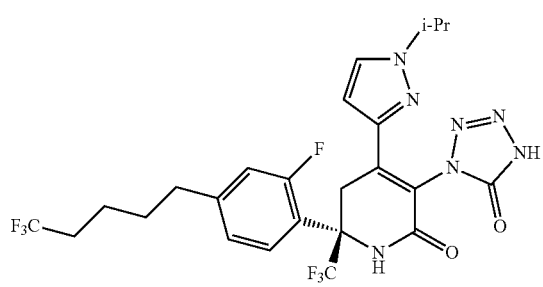<br>(S)-6-(2-fluoro-4-(5,5,5-trifluoropentyl)phenyl)-4-(1-isopropyl-1H-pyrazol-3-yl)-3-(5-oxo-4,5-dihydro-1H-tetrazol-1-yl)-6-(trifluoromethyl)-5,6-dihydropyridin-2(1H)-one | $^1$H NMR (500 MHz, DMSO-$d_6$) δ 7.85 (s, 1H), 7.60-7.51 (m, 1H), 7.20-7.09 (m, 2H), 6.08 (d, J = 32.3 Hz, 1H), 4.56-4.46 (m, 1H), 4.36-4.20 (m, 1H), 3.81-3.62 (m, 1H), 2.62 (t, J = 7.6 Hz, 2H), 2.34-2.21 (m, 2H), 1.72-1.59 (m, 2H), 1.53-1.43 (m, 2H), 1.39-1.32 (m, 6H). MS (ESI) m/z: 576.6 (M + H)$^+$. |

TABLE 2-continued

| Example | Structure and Name | Analytical Data |
|---|---|---|
| 11 | 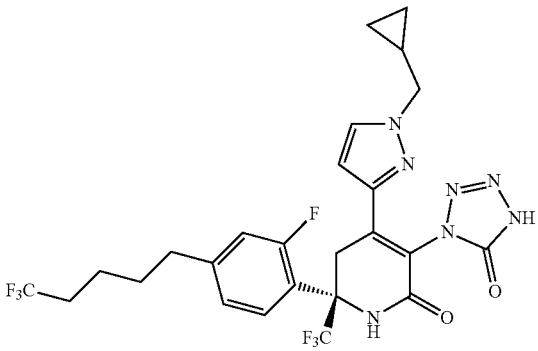<br>(S)-4-(1-(cyclopropylmethyl)-1H-pyrazol-3-yl)-6-(2-fluoro-4-(5,5,5-trifluoropentyl)phenyl)-3-(5-oxo-4,5-dihydro-1H-tetrazol-1-yl)-6-(trifluoromethyl)-5,6-dihydropyridin-2(1H)-one | $^1$H NMR (500 MHz, DMSO-$d_6$) δ 7.79 (br. S., 1H), 7.52-7.43 (m, 1H), 7.15-6.99 (m, 2H), 5.94 (d, J = 30.52 Hz, 1H), 4.33-4.15 (m, 1H), 4.00-3.86 (m, 2H), 3.76-3.58 (m, 1H), 3.47-3.36 (m, 1H), 2.56 (t, J = 6.9 Hz, 2H), 2.26-2.13 (m, 2H), 1.63-1.53 (m, 2H), 1.47-1.36 (m, 2H), 0.49-0.41 (m, 2H), 0.34-0.24 (m, 2H). MS (ESI) m/z: 588.5 (M + H)$^+$. |
| 12 | 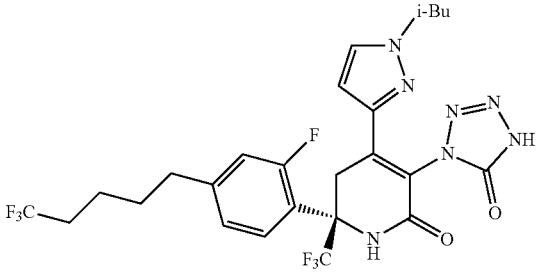<br>(S)-6-(2-fluoro-4-(5,5,5-trifluoropentyl)phenyl)-4-(1-isopropyl-1H-pyrazol-3-yl)-3-(5-oxo-4,5-dihydro-1H-tetrazol-1-yl)-6-(trifluoromethyl)-5,6-dihydropyridin-2(1H)-one | $^1$H NMR (500 MHz, DMSO-$d_6$) δ 7.72 (br. s., 1H), 7.50-7.43 (m, 1H), 7.12-7.01 (m, 2H), 5.94 (d, J = 32.4 Hz 1H), 4.33-4.15 (m, 1H), 3.92-3.84 (m, 2H), 3.74-3.58 (m, 1H), 2.55 (t, J = 7.5 Hz, 2H), 2.24-2.12 (m, 2H), 2.03-1.93 (m, 1H), 1.63-1.52 (m, 2H), 1.46-1.35 (m, 2H), 0.78-0.70 (m, 6H). MS (ESI) m/z: 590.5 (M + H)$^+$. |
| 13 | 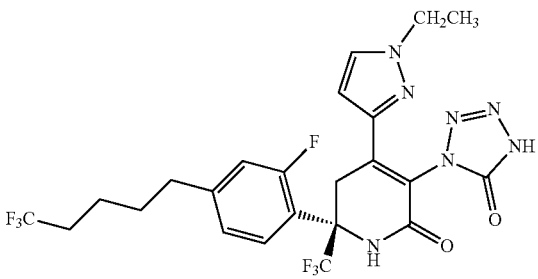<br>(S)-4-(1-ethyl-1H-pyrazol-3-yl)-6-(2-fluoro-4-(5,5,5-trifluoropentyl)phenyl)-3-(5-oxo-4,5-dihydro-1H-tetrazol-1-yl)-6-(trifluoromethyl)-5,6-dihydropyridin-2(1H)-one | $^1$H NMR (500 MHz, DMSO-$d_6$) δ 7.77 (br. s., 1H), 7.57-7.46 (m, 1H), 7.17-7.06 (m, 2H), 5.91 (d, J = 15.6 Hz, 1H), 4.34-4.18 (m, 1H), 4.16-4.07 (m, 2H), 3.71-3.51 (m, 1H), 2.60 (t, J = 7.6Hz, 2H), 2.30-2.16 (m, 2H), 1.67-1.56 (m, 2H), 1.51-1.40 (m, 2H), 1.36-1.27 (m, 3H). MS (ESI) m/z: 562.5 (M + H)$^+$. |

TABLE 2-continued

| Example | Structure and Name | Analytical Data |
|---|---|---|
| 14 | 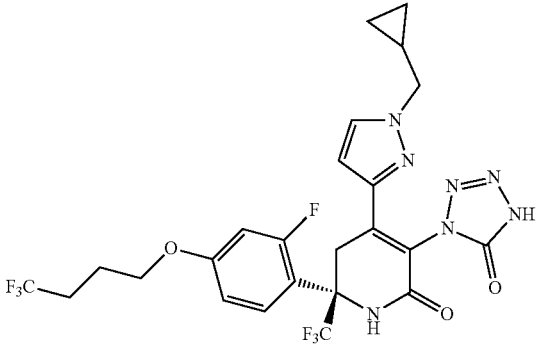<br>(S)-4-(1-(cyclopropylmethyl)-1H-pyrazol-3-yl)-6-(2-fluoro-4-(4,4,4-trifluorobutoxy)phenyl)-3-(5-oxo-4,5-dihydro-1H-tetrazol-1-yl)-6-(trifluoromethyl)-5,6-dihydropyridin-2(1H)-one | $^1$H NMR (500 MHz, DMSO-$d_6$) δ 7.80 (s, 1H), 7.57-7.45 (m, 1H), 6.93-6.80 (m, 2H), 5.97 (d, J = 23.2 Hz, 1H), 4.40-4.18 (m, 1H), 4.04 (t, J = 6.0 Hz, 2H), 3.88-3.85 (m, 2H), 3.74-3.58 (m, 1H), 2.44-2.30 (m, 2H), 1.98-1.86 (m, 2H), 1.21-1.10 (m, 1H), 0.55-0.46 (m, 2H), 0.36-0.28 (m, 2H). MS (ESI) m/z: 590.5 (M + H)$^+$. |
| 15 | 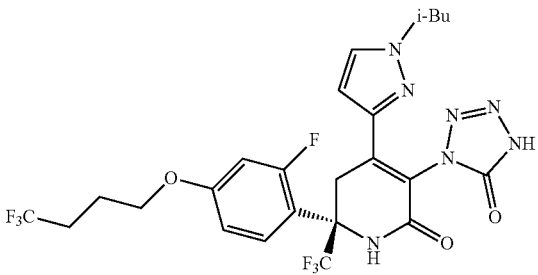<br>(S)-6-(2-fluoro-4-(4,4,4-trifluoropentyl)phenyl)-4-(1-isopropyl-1H-pyrazol-3-yl)-3-(5-oxo-4,5-dihydro-1H-tetrazol-1-yl)-6-(trifluoromethyl)-5,6-dihydropyridin-2(1H)-one | $^1$H NMR (500 MHz, DMSO-$d_6$) δ 7.79 (s, 1H), 7.59-7.45 (m, 1H), 6.99-6.81 (m, 2H), 5.95 (d, J = 24.4 Hz, 1H), 4.38-4.21 (m, 1H), 4.07 (t, J = 6.0 Hz, 2H), 4.00-3.90 (m, 2H), 3.65 (d, J = 17.4 Hz, 1H), 2.47-2.32 (m, 2H), 2.14-2.01 (m, 1H), 1.93 (br. s., 2H), 0.87-0.75 (m, 6H). MS (ESI) m/z: 592.5 (M + H)$^+$. |
| 16 | 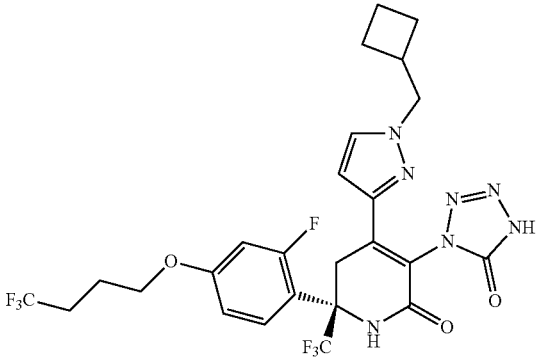<br>(S)-4-(1-(cyclobutylmethyl)-1H-pyrazol-3-yl)-6-(2-fluoro-4-(4,4,4-trifluorobutoxy)phenyl)-3-(5-oxo-4,5-dihydro-1H-tetrazol-1-yl)-6-(trifluoromethyl)-5,6-dihydropyridin-2(1H)-one | $^1$H NMR (500 MHz, DMSO-$d_6$) δ 7.71 (s, 1H), 7.52-7.40 (m, 1H), 6.91-6.76 (m, 2H), 5.93 (d, J = 25.0 Hz, 1H), 4.31-4.17 (m, 1H), 4.11-4.06 (m, 2H), 4.01 (t, J = 6.0Hz, 2H), 3.72-3.53 (m, 1H), 2.68-2.58 (m, 1H), 2.41-2.26 (m, 2H), 1.89 (m, 4H), 1.84-1.72 (m, 2H), 1.71-1.62 (m,2H). MS (ESI) m/z: 604.6 (M + H)$^+$. |

TABLE 2-continued

| Example | Structure and Name | Analytical Data |
|---|---|---|
| 17 | 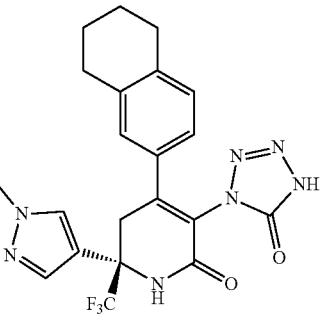<br>(S)-3-(5-oxo-4,5-dihydro-1H-tetrazol-1-yl)-4-(5,6,7,8-tetrahydronaphthalen-2-yl)-6-(1-(7,7,7-trifluoroheptyl)-1H-pyrazol-4-yl)-6-(trifluoromethyl)-5,6-dihydropyridin-2(1H)-one | $^1$H NMR (500 MHz, DMSO-$d_6$) δ 7.96 (s, 1H), 7.67 (d, J = 6.7 Hz, 1H), 7.27 (d, J = 7.9 Hz, 1H), 7.11 (s, 1H), 7.04 (br. s., 1H), 6.98 (d, J = 7.6 Hz, 1H), 4.11-4.04 (m, 2H), 3.71-3.58 (m., 4H), 2.75-2.55 (m, 2H), 2.19-2.06 (m, 2H), 1.86-1.58 (m, 6H), 1.43-1.33 (m, 2H), 1.33-1.24 (m, 2H), 1.21-1.08 (m, 2H). MS (ESI) m/z: 598.6 (M + H)$^+$. |
| 18 | 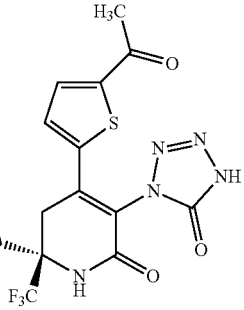<br>(S)-4-(5-acetylthiophen-2-yl)-3-(5-oxo-4,5-dihydro-1H-tetrazol-1-yl)-6-(4-(4,4,4-trifluorobutoxy)phenyl)-6-(trifluoromethyl)-5,6-dihydropyridin-2(1H)-one | $^1$H NMR (400 MHz, chloroform-d) δ 7.60 (d, J = 3.96 Hz, 1H), 7.44 (br. s., 2H), 7.33 (d, J = 3.08 Hz, 1H), 6.93 (d, J = 8.80 Hz, 2H), 4.01 (t, J = 5.83 Hz, 2H), 3.78-3.94 (m, 1H), 3.63-3.76 (m, 1H), 2.53 (s, 3H), 2.22-2.40 (m, 2H), 1.99-2.10 (m, 2H). MS (ESI)/m/z: 576.3 (M + H)$^+$. |
| 19 | 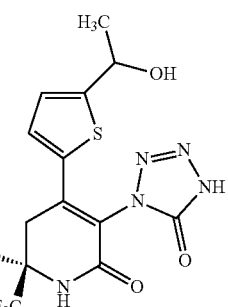<br>(6S)-4-(5-(1-hydroxyethyl)thiophen-2-yl)-3-(5-oxo-4,5-dihydro-1H-tetrazol-1-yl)-6-(4-(4,4,4-trifluorobutoxy)phenyl)-6-(trifluoromethyl)-5,6-dihydropyridin-2(1H)-one (diastereomeric mixture) | $^1$H NMR (400 MHz, methanol-$d_4$) δ 7.67 (dd, J = 3.96, 14.53 Hz, 1H), 7.51-7.63 (m, 2H), 7.00-7.05 (m, 1H), 6.98 (d, J = 9.02 Hz, 2H), 4.93-5.03 (m, 1H), 4.05 (t, J = 6.05 Hz, 2H), 3.75-4.02 (m, 2H), 2.27-2.44 (m, 2H), 1.94-2.08 (m, 2H), 1.40-1.50 (m, 3H). MS (ESI) m/z: 578.3 (M + H)$^+$. |

TABLE 2-continued

| Example | Structure and Name | Analytical Data |
|---|---|---|
| 20 | 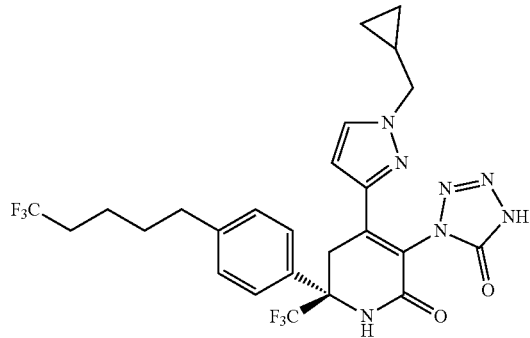<br>(S)-4-(1-(cyclopropylmethyl)-1H-pyrazol-3-yl)-3-(5-oxo-4,5-dihydro-1H-tetrazol-1-yl)-6-(trifluoromethyl)-6-(4-(5,5,5-trifluoropentyl)phenyl)-5,6-dihydropyridin-2(1H)-one | $^1$H NMR (500 MHz, DMSO-$d_6$) δ 7.84 (s, 1H), 7.63-7.52 (m, 2H), 7.35-7.22 (m, 2H), 6.19-6.01 (m, 1H), 4.03-3.91 (m, 2H), 2.60 (t, J = 7.6 Hz, 2H), 2.35-2.16 (m, 2H), 1.63 (quin, J = 7.3 Hz, 2H), 1.48 (d, J = 3.4 Hz, 2H), 1.26-1.12 (m, 1H), 0.51 (d, J = 7.6 Hz, 2H), 0.35 (br. s., 2H). MS (ESI) m/z: 570.2 (M + H)$^+$. |
| 21 | 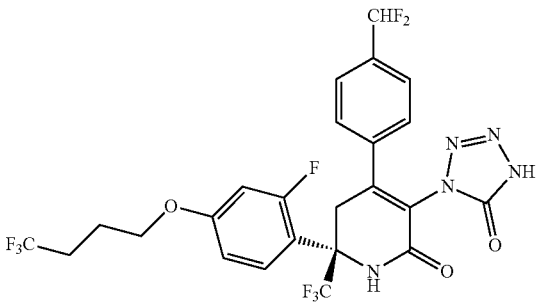<br>(S)-4-(4-(difluoromethyl)phenyl)-6-(2-fluoro-4-(4,4,4-trifluorobutoxy)phenyl)-3-(5-oxo-4,5-dihydro-1H-tetrazol-1-yl)-6-(trifluoromethyl)-5,6-dihydropyridin-2(1H)-one | $^1$H NMR (500 MHz, DMSO) δ 7.64-7.47 (m, 3H), 7.32 (d, J = 7.6 Hz, 2H), 7.16-6.82 (m, 3H), 4.08 (br. s., 2H), 4.00-3.75 (m, 2H), 2.40 (dd, J = 16.5, 11.0 Hz, 2H), 1.92 (d, J = 7.0 Hz, 2H). MS (ESI) m/z: 596.1 (M + H)$^+$. |
| 22 | 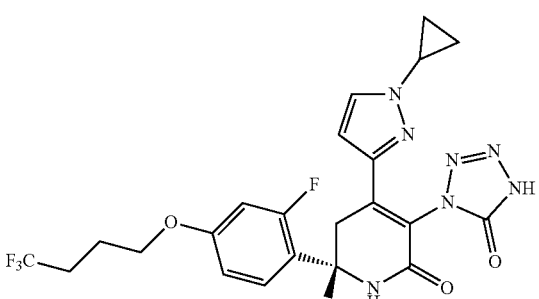<br>(S)-4-(5-cyclopropylthiazol-2-yl)-6-(2-fluoro-4-(4,4,4-trifluorobutoxy)phenyl)-3-(5-oxo-4,5-dihydro-1H-tetrazol-1-yl)-6-(trifluoromethyl)-5,6-dihydropyridin-2(1H)-one | $^1$H NMR (500 MHz, DMSO-$d_6$) δ 7.85 (s, 1H), 7.49 (t, J = 9.2 Hz, 1H), 6.96-6.81 (m, 2H), 4.56-4.39 (m, 1H), 4.06 (t, J = 5.6 Hz, 2H), 3.91-3.71 (m, 1H), 2.43-2.33 (m, 2H), 2.20 (br. s., 1H), 2.00-1.86 (m, 2H), 1.08 (d, J = 6.4 Hz, 2H), 0.74 (d, J = 4.3 Hz, 2H). MS (ESI) m/z: 593.1 (M + H)$^+$. |

TABLE 2-continued

| Example | Structure and Name | Analytical Data |
|---|---|---|
| 23 | 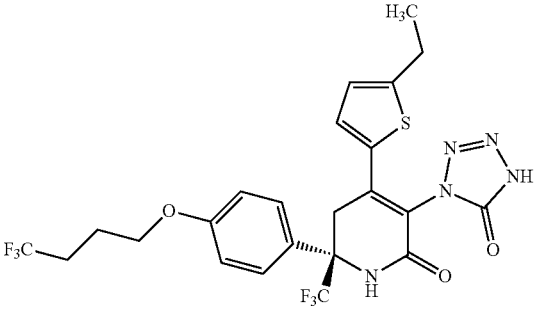<br>(S)-4-(5-ethylthiophen-2-yl)-3-(5-oxo-4,5-dihydro-1H-tetrazol-1-yl)-6-6(4,4,4-trifluorobutoxy)phenyl)-6-(trifluoromethyl)-5,6-dihydropyridin-2(1H)-one | $^1$H NMR (400 MHz. methanol-$d_4$) δ 7.53-7.69 (m, 3H), 6.98 (d, J = 8.80 Hz, 2H), 6.88-6.94 (m, 1H), 4.05 (t, J = 5.94 Hz, 2H), 3.74-4.02 (m, 2H), 2.81 (dq, J = 2.97, 7.45 Hz, 2H), 2.28-2.43 (m, 2H), 1.96-2.06 (m, 2H), 1.20-1.27 (m, 3H). MS (ESI) m/z: 562.1 (M + H)$^+$. |
| 24 | 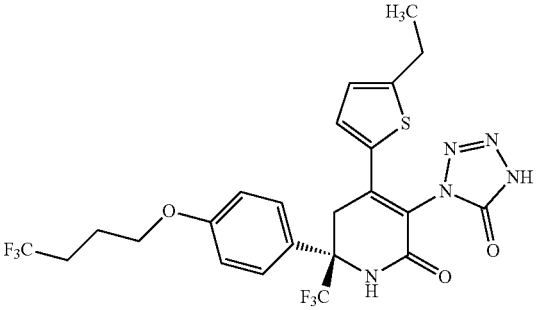<br>(S)-6-(2-chloro-4-(4,4,4-trifluorobutoxy)phenyl)-4-(5-ethylthiophen-2-yl)-3-(5-oxo-4,5-dihydro-1H-tetrazol-1-yl)-5,6-dihydropyridin-2(1H)-one | $^1$H NMR (400 MHz, methanol-$d_4$) δ 7.49-7.65 (m, 1H), 7.34-7.40 (m, 1H), 7.06 (dd, J = 2.53, 7.15 Hz, 1H), 6.98 (ddd, J = 2.53, 6.33, 8.75 Hz, 1H), 6.86 (t, J = 3.63 Hz, 1H), 5.37 (ddd, J = 5.94, 8.31, 12.16 Hz, 1H), 4.02-4.10 (m, 2H), 3.55 (td, J = 6.38, 16.95 Hz, 1H), 3.32-3.36 (m, 1H), 2.77-2.86 (m, 2H), 2.28-2.43 (m, 2H), 1.97-2.07 (m, 2H), 1.24 (t, J = 7.37 Hz, 3H). MS (ESI) m/z: 528.1 (M + H)$^+$. |

What is claimed is:

1. A compound of Formula (I):

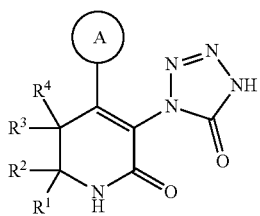

or a stereoisomer, a tautomer, a pharmaceutically acceptable salt, a polymorph, a solvate or a hydrate thereof, wherein:

ring A is independently phenyl substituted with 0-1 $R^6$ and 0-2 $R^7$;

$R^1$ is independently selected from: —(CH$_2$)$_m$—(C$_{3-6}$ carbocycle substituted with 0-2 $R^b$ and 0-2 $R^g$), —(CH$_2$)$_m$-(5- to 6-membered heteroaryl comprising carbon atoms and 1-4 heteroatoms selected from N, NR$^e$, O and S; wherein said heteroaryl is substituted with 0-1 $R^b$ and 0-2 $R^g$), and (a C$_{1-12}$ hydrocarbon chain substituted with 0-3 $R^a$; wherein said hydrocarbon chain may be straight or branched, saturated or unsaturated);

$R^2$ is independently selected from: C$_{1-4}$ alkyl, C$_{3-4}$ cycloalkyl, and C$_{1-4}$ haloalkyl;

$R^3$ is independently selected from: H, F, C$_{1-4}$ alkyl and CN;

$R^4$ is independently selected from: H, F, and C$_{1-4}$ alkyl;

$R^3$ and $R^4$ may be combined with the carbon atom to which they are attached to form a 3- to 6-membered carbocycle;

$R^6$ is independently selected from: halogen, C$_{1-6}$ alkyl substituted with 0-2 $R^h$, C$_{1-4}$ alkoxy, C$_{1-4}$ haloalkyl, C$_{1-4}$ haloalkoxy, CO(C$_{1-4}$ alkyl), —(CH$_2$)$_m$—C$_{3-6}$ carbocycle, —(CH$_2$)$_m$—NR$^i$R$^i$, CN, OR$^i$, SR$^i$, and (a 4- to 6-membered heterocycle comprising carbon atoms and 1-4 heteroatoms selected from N, NR$^e$, O, and S);

$R^7$ is independently selected from: halogen, C$_{1-4}$ alkyl, C$_{1-4}$ alkoxy, C$_{1-4}$ haloalkyl, and C$_{1-4}$ haloalkoxy;

alternatively, $R^6$ and $R^7$, together with the carbon atoms to which they are attached, combine to form a 5- to 6-membered carbocyclic ring or a 5- to 6-membered heterocyclic ring comprising carbon atoms and 1-3 heteroatoms selected from N, NR$^e$, O, and S; wherein said heterocycle is substituted with 0-2 $R^g$;

$R^a$ is, at each occurrence, independently selected from: halogen, OH, C$_{1-6}$ alkoxy, C$_{1-6}$ haloalkyl, C$_{1-6}$ haloalkoxy, N(C$_{1-4}$ alkyl)$_2$, COOH, and —(CH$_2$)$_n$—R;

$R^b$ is, at each occurrence, independently selected from: halogen, OH, C$_{1-10}$ alkyl, C$_{1-10}$ alkoxy, C$_{1-10}$ haloalkyl, C$_{1-10}$ haloalkoxy, C$_{1-10}$ alkylthio, C$_{1-10}$ haloalkylthio, N(C$_{1-4}$ alkyl)$_2$, —CONH(C$_{4-20}$ alkyl), —CONH(C$_{4-20}$ haloalkyl), —O(CH$_2$)$_s$O(C$_{1-6}$ alkyl), —O(CH$_2$)$_s$O(C$_{1-6}$ haloalkyl), $R^c$, and —(CH$_2$)$_n$—(O)$_t$—(CH$_2$)$_m$R$^c$;

$R^c$ is, at each occurrence, independently selected from: C$_{3-6}$ cycloalkyl substituted with 0-2 $R^d$, C$_{3-6}$ cycloalkenyl substituted with 0-2 $R^d$, —(CH$_2$)$_m$-(phenyl substituted with 0-3 $R^d$), and (a 5- to 6-membered heterocycle comprising carbon atoms and 1-4 heteroatoms selected from N, NR$^e$, O, and S; wherein said heterocycle is substituted with 0-2 $R^d$);

$R^d$ is, at each occurrence, independently selected from: halogen, OH, CN, NO$_2$, C$_{1-4}$ alkyl, C$_{1-4}$ alkoxy, C$_{1-4}$ haloalkyl, C$_{1-4}$ haloalkoxy, tetrazolyl, OBn and phenyl;

$R^e$ is, at each occurrence, independently selected from: H, C$_{1-8}$ alkyl, C$_{1-8}$ haloalkyl, —(CH$_2$)$_n$—C$_{3-6}$ carbocycle, CO(C$_{1-4}$ alkyl) and COBn;

$R^f$ is, at each occurrence, independently selected from: H and C$_{1-4}$ alkyl;

$R^g$ is, at each occurrence, independently selected from: halogen, C$_{1-4}$ alkyl, C$_{1-4}$ alkoxy, C$_{1-4}$ haloalkyl, and C$_{1-4}$ haloalkoxy;

$R^h$ is, at each occurrence, independently selected from: OH, halogen, C$_{1-4}$ alkyl, C$_{1-4}$ alkoxy, C$_{1-4}$ haloalkyl, and C$_{1-4}$ haloalkoxy;

$R^i$ is, at each occurrence, independently selected from the group consisting of C$_{1-4}$ alkyl, C$_{3-4}$ cycloalkyl and phenyl;

n, at each occurrence, is independently 0 or 1;

m, at each occurrence, is independently 0, 1, 2, 3, or 4;

s, at each occurrence, is independently 1, 2, or 3; and t, at each occurrence, is independently 0 or 1.

2. A compound according to claim 1, wherein:

$R^1$ is independently selected from: (C$_{3-6}$ carbocycle substituted with 0-2 $R^b$ and 0-2 $R^g$), and (a 5- to 6-membered heteroaryl comprising carbon atoms and 1-4 heteroatoms selected from N, NR$^e$, O and S; wherein said heteroaryl is substituted with 0-1 $R^b$ and 0-2 $R^g$);

$R^3$ is independently selected from: H, F, C$_{1-4}$ alkyl and CN;

$R^4$ is independently selected from: H, F, and C$_{1-4}$ alkyl;

$R^b$ is, at each occurrence, independently selected from: halogen, C$_{1-10}$ alkyl, C$_{1-10}$ alkoxy, C$_{1-10}$ haloalkyl, C$_{1-10}$ haloalkoxy, C$_{1-10}$ alkylthio, C$_{1-10}$ haloalkylthio, N(C$_{1-4}$ alkyl)$_2$, —CONH(C$_{4-20}$ alkyl), —CONH(C$_{1-6}$ haloalkyl), —O(CH$_2$)$_s$O(C$_{1-6}$ alkyl), —O(CH$_2$)$_s$O(C$_{1-6}$ haloalkyl), $R^c$, and —(CH$_2$)$_n$—(O)$_t$—(CH$_2$)$_m$$R^c$; and $R^d$ is, at each occurrence, independently selected from: halogen, C$_{1-4}$ alkyl, C$_{1-4}$ alkoxy, C$_{1-4}$ haloalkyl, C$_{1-4}$ haloalkoxy, tetrazolyl, OBn and phenyl.

3. A compound according to claim 1, wherein:

ring A is independently selected from phenyl substituted with 0-1 $R^6$ and 0-2 $R^7$; and alternatively, $R^6$ and $R^7$, together with the carbon atoms to which they are attached, combine to form a 6-membered carbocyclic ring.

4. A compound according to claim 1, wherein:

ring A is independently

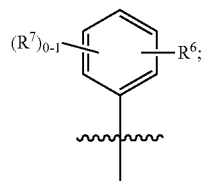

$R^1$ is independently selected from: (phenyl substituted with 1 $R^b$ and 0-2 $R^g$), and (a 5-membered heteroaryl comprising carbon atoms and 1-2 heteroatoms selected from N, NR$^e$, O and S; wherein said heteroaryl is substituted with 0-1 $R^b$ and 0-2 $R^g$);

$R^2$ is independently selected from: C$_{1-4}$ alkyl and C$_{1-4}$ haloalkyl;

$R^6$ is independently selected from: halogen, C$_{1-6}$ alkyl with 0-1 OH, C$_{1-4}$ alkoxy, C$_{1-4}$ haloalkoxy, CO(C$_{1-4}$ alkyl), N(C$_{1-4}$ alkyl)$_2$, and —(CH$_2$)$_{0-1}$—C$_{3-6}$ cycloalkyl;

$R^7$ is independently selected from: halogen, C$_{1-4}$ alkyl and C$_{1-4}$ alkoxy;

alternatively, $R^6$ and $R^7$, together with the carbon atoms to which they are attached, combine to form a 6-membered carbocyclic ring;

$R^b$ is, at each occurrence, independently selected from: halogen, C$_{1-8}$ alkyl, C$_{1-8}$ alkoxy, C$_{1-8}$ haloalkyl, C$_{1-10}$ haloalkoxy, and phenoxy;

$R^e$ is, at each occurrence, independently selected from: C$_{1-6}$ alkyl, C$_{1-8}$ haloalkyl, and —(CH$_2$)$_n$—C$_{3-6}$ carbocycle; and $R^g$ is, at each occurrence, independently selected from: halogen, C$_{1-4}$ alkyl, C$_{1-4}$ alkoxy, C$_{1-4}$ haloalkyl, and C$_{1-4}$ haloalkoxy.

5. A compound of Formula (IIa):

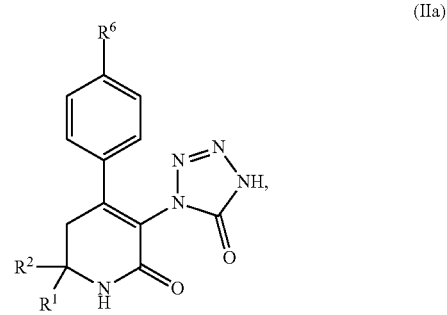

or a stereoisomer, a tautomer, a pharmaceutically acceptable salt, a polymorph, a solvate or a hydrate thereof, wherein:

$R^1$ is independently selected from:

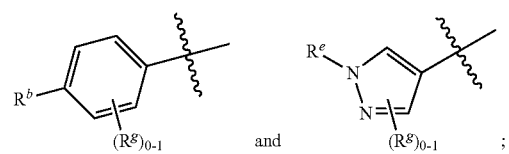

$R^2$ is independently selected from: CF$_3$ and CH$_3$;

$R^6$ is independently selected from: halogen, C$_{1-4}$ alkyl substituted with 0-1 OH, C$_{1-4}$ alkoxy, C$_{1-4}$ haloalkoxy, CO(C$_{1-4}$ alkyl), and —(CH$_2$)$_{0-1}$—C$_{3-4}$ cycloalkyl;

$R^b$ is independently selected from: —(CH$_2$)$_{1-6}$CF$_3$, —(CH$_2$)$_{1-4}$CF$_2$CF$_3$, —O(CH$_2$)$_{1-6}$CF$_3$, and —O(CH$_2$)$_{1-4}$CF$_2$CF$_3$;

$R^e$ is, at each occurrence, independently selected from: C$_{1-4}$ alkyl, —(CH$_2$)$_{1-6}$CF$_3$, and —(CH$_2$)$_{0-1}$—C$_{3-4}$ cycloalkyl; and $R^g$ is independently halogen.

6. A compound according to claim 5, wherein:
R¹ is
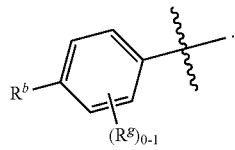
7. A compound according to claim 1, wherein the compound is selected from:
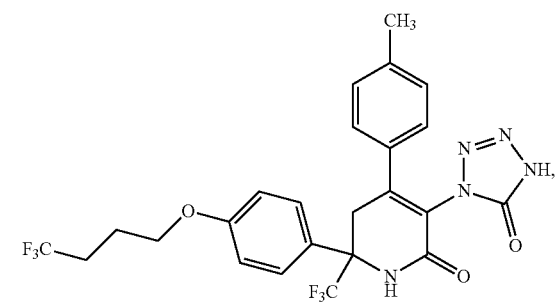 [SMILES: O=C1NC(c2ccc(OCCCC(F)(F)F)cc2F)(C(F)(F)F)CC(c2ccc(C(F)F)cc2)=C1n1nn[nH]c1=O]
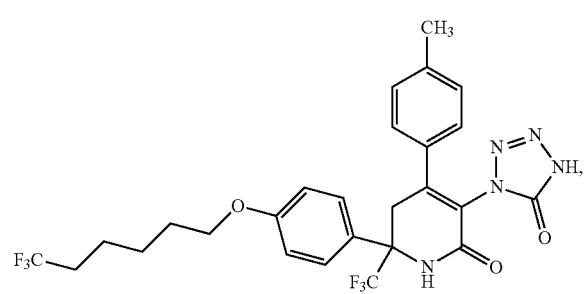
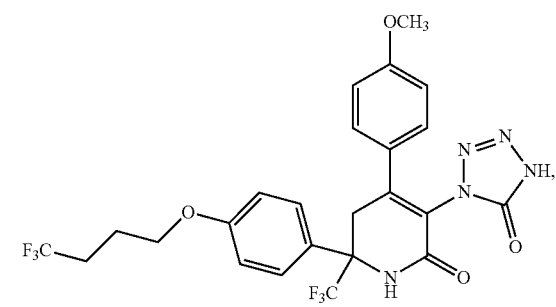
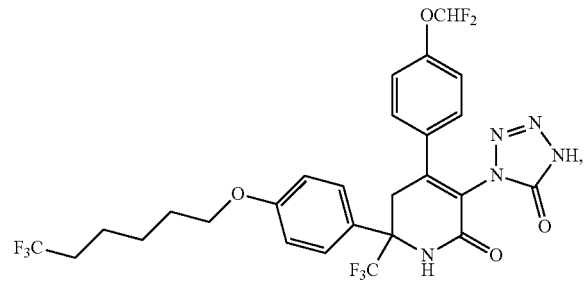
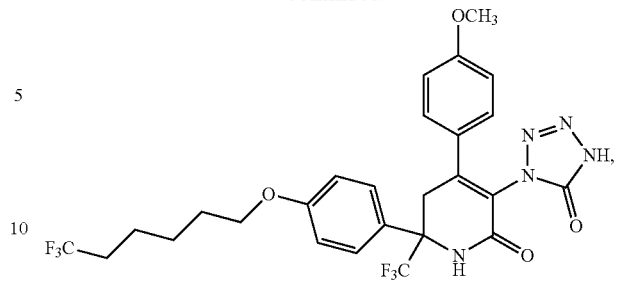
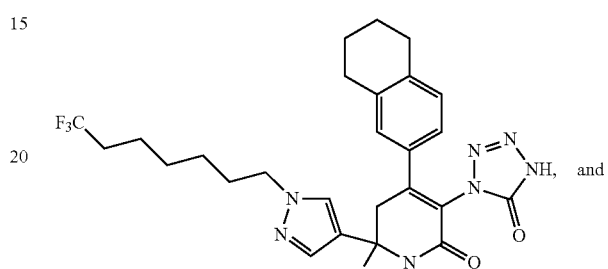
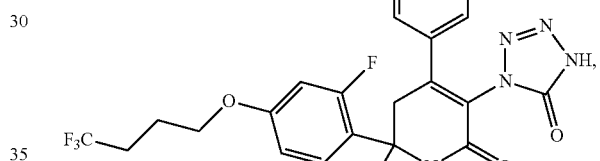
or a stereoisomer, a tautomer, a pharmaceutically acceptable salt, a polymorph, a solvate or a hydrate thereof.
8. A compound according to claim 1, wherein the compound is selected from:
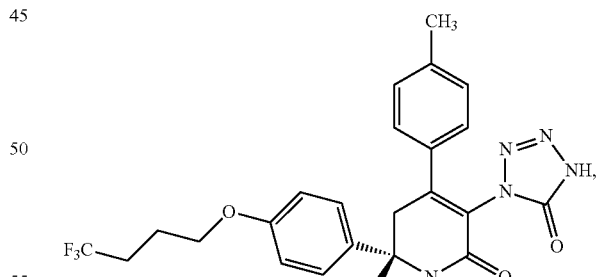
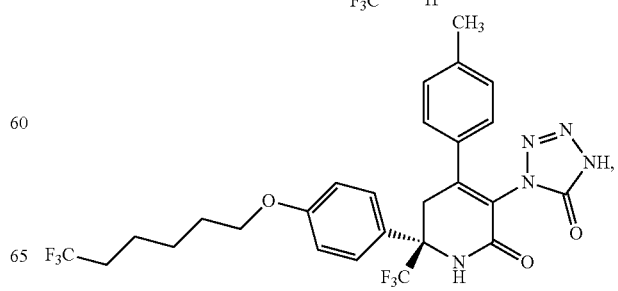

-continued

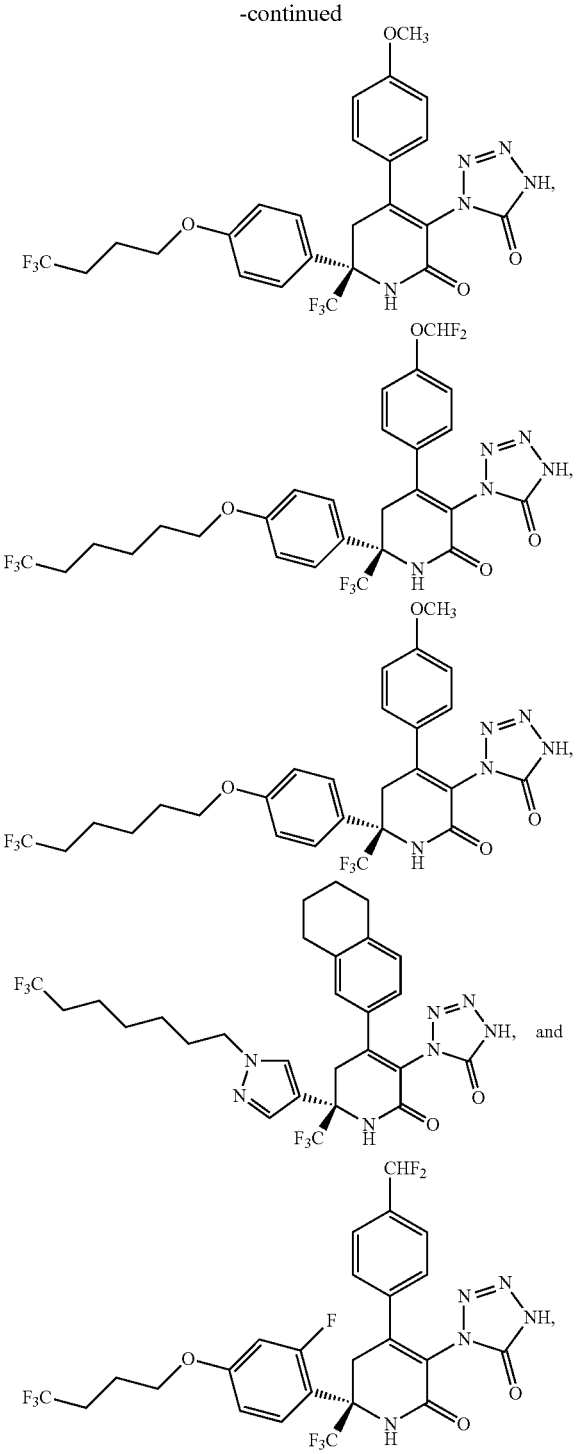

or an enantiomer, a tautomer, a pharmaceutically acceptable salt, a polymorph, a solvate or a hydrate thereof.

9. A pharmaceutical composition, comprising a pharmaceutically acceptable carrier and a compound of claim 1.

10. A pharmaceutical composition, comprising a pharmaceutically acceptable carrier and a compound of claim 5.

11. A pharmaceutical composition, comprising a pharmaceutically acceptable carrier and a compound of claim 6.

12. A pharmaceutical composition, comprising a pharmaceutically acceptable carrier and a compound of claim 7.

13. A pharmaceutical composition, comprising a pharmaceutically acceptable carrier and a compound of claim 8.

14. A pharmaceutical composition comprising a compound according to claim 1 and further comprising a dipeptidyl peptidase-IV (DPP4) inhibitor.

15. A pharmaceutical composition comprising a compound according to claim 5 and further comprising a dipeptidyl peptidase-IV (DPP4) inhibitor.

16. A pharmaceutical composition comprising a compound according to claim 7 and further comprising a dipeptidyl peptidase-IV (DPP4) inhibitor.

17. A pharmaceutical composition comprising a compound according to claim 8 and further comprising a dipeptidyl peptidase-IV (DPP4) inhibitor.

18. A method for the treatment of diabetes, hyperglycemia, impaired glucose tolerance, gestational diabetes, insulin resistance, hyperinsulinemia, nonalcoholic fatty liver disease, nonalcoholic steatohepatitis, Metabolic Syndrome, obesity, dyslipidemia, and/or glaucoma comprising administering to a patient in need of such treatment a therapeutically effective amount of at least a compound according to claim 1.

19. A method for the treatment of diabetes, hyperglycemia, impaired glucose tolerance, gestational diabetes, insulin resistance, hyperinsulinemia, nonalcoholic fatty liver disease, nonalcoholic steatohepatitis, Metabolic Syndrome, obesity, dyslipidemia, and/or glaucoma comprising administering to a patient in need of such treatment a therapeutically effective amount of at least a compound according to claim 5.

20. A method for the treatment of diabetes, hyperglycemia, impaired glucose tolerance, gestational diabetes, insulin resistance, hyperinsulinemia, nonalcoholic fatty liver disease, nonalcoholic steatohepatitis, Metabolic Syndrome, obesity, dyslipidemia, and/or glaucoma comprising administering to a patient in need of such treatment a therapeutically effective amount of at least a compound according to claim 6.

21. A method for the treatment of diabetes, hyperglycemia, impaired glucose tolerance, gestational diabetes, insulin resistance, hyperinsulinemia, nonalcoholic fatty liver disease, nonalcoholic steatohepatitis, Metabolic Syndrome, obesity, dyslipidemia, and/or glaucoma comprising administering to a patient in need of such treatment a therapeutically effective amount of at least a compound according to claim 7.

22. A method for the treatment of diabetes, hyperglycemia, impaired glucose tolerance, gestational diabetes, insulin resistance, hyperinsulinemia, nonalcoholic fatty liver disease, nonalcoholic steatohepatitis, Metabolic Syndrome, obesity, dyslipidemia, and/or glaucoma comprising administering to a patient in need of such treatment a therapeutically effective amount of at least a compound according to claim 8.

* * * * *

UNITED STATES PATENT AND TRADEMARK OFFICE
CERTIFICATE OF CORRECTION

PATENT NO.         : 10,329,273 B2
APPLICATION NO.    : 16/117107
DATED              : June 25, 2019
INVENTOR(S)        : Saleem Ahmad It is certified that error appears in the above-identified patent and that said Letters Patent is hereby corrected as shown below:

On the Title Page

Item (63): Column 1
Line 6-7, "Mar. 15, 2015" should read -- Mar. 5, 2015, --.

In the Claims

Column 58
Line 59, Claim 1 "—R;" should read -- —$R^c$; --.

Signed and Sealed this
Tenth Day of September, 2019

Andrei Iancu
*Director of the United States Patent and Trademark Office*